(12) United States Patent
Foresti et al.

(10) Patent No.: US 11,498,332 B2
(45) Date of Patent: Nov. 15, 2022

(54) APPARATUS AND METHOD FOR ACOUSTOPHORETIC PRINTING

(71) Applicant: President and Fellows of Harvard College, Cambridge, MA (US)

(72) Inventors: Daniele Foresti, Somerville, MA (US); Jennifer A. Lewis, Cambridge, MA (US); Armand Kurum, Cambridge, MA (US)

(73) Assignee: PRESIDENT AND FELLOWS OF HARVARD COLLEGE, Cambridge, MA (US)

( * ) Notice: Subject to any disclaimer, the term of this patent is extended or adjusted under 35 U.S.C. 154(b) by 711 days.

(21) Appl. No.: 16/320,746

(22) PCT Filed: Jul. 24, 2017

(86) PCT No.: PCT/US2017/043539
§ 371 (c)(1),
(2) Date: Jan. 25, 2019

(87) PCT Pub. No.: WO2018/022513
PCT Pub. Date: Feb. 1, 2018

(65) Prior Publication Data
US 2019/0160813 A1 May 30, 2019

Related U.S. Application Data

(60) Provisional application No. 62/367,318, filed on Jul. 27, 2016.

(51) Int. Cl.
*B41J 2/14* (2006.01)
*B33Y 10/00* (2015.01)
(Continued)

(52) U.S. Cl.
CPC ............ *B41J 2/14008* (2013.01); *A23G 1/54* (2013.01); *A23P 20/20* (2016.08); *A61L 27/24* (2013.01);
(Continued)

(58) Field of Classification Search
CPC ....... B41J 2/14; B41J 2/14008; B29C 64/112; B29C 64/209; B33Y 10/00; B33Y 30/00;
(Continued)

(56) References Cited

U.S. PATENT DOCUMENTS 5,880,759 A 3/1999 Silverbrook
6,003,388 A 12/1999 Oeftering
(Continued)

FOREIGN PATENT DOCUMENTS

WO WO 2014/029505 A1 2/2014
WO WO 2015/110600 A1 7/2015

OTHER PUBLICATIONS

Extended European Search Report, issued in EP Application No. 17835062.5, dated Feb. 20, 2020, pp. 1-10, European Patent Office, Munich, Germany.
(Continued)

*Primary Examiner* — Ericson M Lachica
(74) *Attorney, Agent, or Firm* — Crowell & Moring LLP

(57) ABSTRACT

A method of acoustophoretic printing comprises generating an acoustic field at a first end of an acoustic chamber fully or partially enclosed by sound-reflecting walls. The acoustic field interacts with the sound-reflecting walls and travels through the acoustic chamber. The acoustic field is enhanced in a chamber outlet at a second end of the acoustic chamber. An ink is delivered into a nozzle positioned within the acoustic chamber. The nozzle has a nozzle opening projecting into the chamber outlet. The ink travels through the nozzle and is exposed to the enhanced acoustic field at the
(Continued)

nozzle opening, and a predetermined volume of the ink is ejected from the nozzle opening and out of the acoustic chamber.

14 Claims, 23 Drawing Sheets

(51) Int. Cl.
| | |
|---|---|
| B33Y 30/00 | (2015.01) |
| B33Y 70/00 | (2020.01) |
| B29C 64/00 | (2017.01) |
| A23P 20/20 | (2016.01) |
| A23G 1/50 | (2006.01) |
| A61L 27/00 | (2006.01) |
| B41M 5/00 | (2006.01) |
| C09D 11/50 | (2014.01) |
| B29C 64/112 | (2017.01) |
| B29C 64/209 | (2017.01) |
| A23G 1/54 | (2006.01) |
| A61L 27/24 | (2006.01) |
| A61L 27/38 | (2006.01) |
| A61L 27/54 | (2006.01) |
| C09D 11/52 | (2014.01) |
| A23P 20/25 | (2016.01) |

(52) U.S. Cl.
 CPC ........... *A61L 27/3834* (2013.01); *A61L 27/54* (2013.01); *B29C 64/112* (2017.08); *B29C 64/209* (2017.08); *B33Y 10/00* (2014.12); *B33Y 30/00* (2014.12); *B33Y 70/00* (2014.12); *B41M 5/0023* (2013.01); *C09D 11/52* (2013.01); *A23P 2020/253* (2016.08); *A23V 2002/00* (2013.01)

(58) Field of Classification Search
 CPC ......... B33Y 70/00; B33Y 70/10; A23P 20/20; A23P 2020/253; A61L 27/38; A61L 27/54; A61L 27/24; A61L 27/3834; B41M 5/0023; C09D 11/52; A23G 1/54
 See application file for complete search history.

(56) References Cited

U.S. PATENT DOCUMENTS

| | | | |
|---|---|---|---|
| 6,422,690 B1* | 7/2002 | Harvey | B41J 2/14282 |
| | | | 347/68 |
| 7,354,141 B2 | 4/2008 | Elison et al. | |
| 9,878,536 B2 | 1/2018 | Foresti et al. | |
| 2006/0144871 A1 | 7/2006 | Van Tuyl et al. | |
| 2006/0209129 A1 | 9/2006 | Onozawa | |
| 2007/0085867 A1* | 4/2007 | Ishikawa | B41J 2/17513 |
| | | | 347/9 |
| 2007/0231425 A1* | 10/2007 | Ream | A23P 30/00 |
| | | | 426/3 |
| 2009/0115820 A1 | 5/2009 | Nomura et al. | |
| 2014/0097267 A1* | 4/2014 | Shitara | G03G 9/132 |
| | | | 134/99.1 |
| 2015/0037445 A1* | 2/2015 | Murphy | B29C 64/106 |
| | | | 425/131.1 |
| 2015/0118692 A1* | 4/2015 | Johnson | G01N 33/585 |
| | | | 435/7.1 |
| 2016/0367358 A1* | 12/2016 | Tran | A61L 27/3834 |
| 2017/0028721 A1* | 2/2017 | Barbet | B41J 2/02 |

OTHER PUBLICATIONS

First Office Action with English translation, issued in CN Application No. 201780059622.3, dated Mar. 13, 2020, pp. 1-16, China Intellectual Property Administration, Beijing, CN.
International Search Report and Written Opinion for International PCT No. PCTUS/2017/43539, dated Nov. 24, 2017, pp. 1-10.
S. L. N. Ford, "Additive Manufacturing Technology: Potential Implications for U.S. Manufacturing Competitiveness," *Journal of International Commerce and Economics*, Sep. 2014, pp. 1-35.
J. Steele, "The Next Industrial Revolution: Functional Printing," *Printing News*, Apr. 1, 2014, pp. 1-5.
G. D. Martin and I. M. Hutchings, "Fundamentals of Ink Jet Technology," in *Inkjet Technology for Digital Fabrication, First Edition*, John Wiley & Sons (2013) pp. 21-44.
P.K. Kundu, I. M. Cohen and D. R. Dowling, "Conservation Laws," in *Fluid Mechanics*, Elsevier, Inc. (2012) pp. 95-169.
N. Bjelobrk et al., "Contactless transport of acoustically levitated particles," *Applied Physics Letters*, 97 (2010) pp. 161904-1-161904-3.
V. Vandaele et al., "Non-contact handling in microassembly: Acoustical levitation," *Precision Engineering*, 29 (2006) pp. 491-505.
E. H. Brandt, "Levitation in Physics," *Science*, 243 (1989) pp. 349-355.
H. Azhari, "Waves—A General Description," in *Basics of Biomedical Ultrasound for Engineers*, John Wiley & Sons, Inc. (2010) pp. 9-33.
L. V. King, "On the Acoustic Radiation of Pressure on Spheres," *Proceeding of the Royal Society of London*, 147 (1934) p. 212.
D. Foresti et al., "Contactless transport of matter in the first five resonance modes of a line-focused acoustic manipulator," *J. Acoust. Soc. Am.*, 131, 2 (2012) pp. 1029-1038.
J. Christensen et al., "Theory of Resonant Acoustic Transmission through Subwavelength Apertures," *Physical Review Letters*, 101 (2008) pp. 014301-1-014301-4.
B. Hou, "Tuning Fabry-Perot resonances via diffraction evanescent waves," *Physical Review B*, 76 (2007) pp. 054303-1-054303-054303-6.
J. Renner et al., "Reproducibility of DoD Inkjet Printing Systems," 38th International Research Conference, Advances in Printing and Media Technology, Budapest, 2011, pp. 1-8.
D. Foresti et al., "Investigation of a line-focused acoustic levitation for contactless transport of particles," *Journal of Applied Physics*, 109 (2011) pp. 0935503-1-0935503-11.
S. Zhao and J. Wallaschek, "A standing wave acoustic levitation system for large planar objects," *Arch. Appl. Mech*, vol. 81, 2011, pp. 123-139.
D. Foresti and D. Poulikakos, "Acoustophoretic contactless elevation, orbital transport and spinning of matter in air," *Physical Review Letters*, 112 (2014) pp. 024301-1-024301-5.
S. Baer, "Analysis of the particle stability in a new designed ultrasonic levitation device," *Review of Scientific Instruments*, 82 (2011) pp. 105111-1-105111-7.
A. L. Yarin et al., "On the acoustic levitation of droplets," *Journal of Fluid Mechanics*, 356 (1998) pp. 65-91.
Y. Wu, "Development of Free Adjustable Function Generator for Drop-on-Demand Droplets Generation," in *Advances in Intelligent and Soft Computing*, 160, Springer-Verlag (2012) pp. 477-481.
M. Vaezi et al., "A review on 3D micro-additive manufacturing technologies," *Int. Journal of Adv. Manuf. Technol.*, 67 (2012) pp. 1721-1754.
Y. Kim et al., "Design and Fabrication of Electrostatic Inkjet Head using Silicon Micromachining Technology," *Journal of Semiconductor Technology and Science*, 8 (2008) pp. 121-127.
S. Lee et al., "Electrostatic droplet formation and ejection of colloid," *Micro-Nanomechatronics and Human Science*, (2004) pp. 1-6.
M. Colina et al., "Laser-induced forward transfer of liquids: Study of the droplet ejection process," *Journal of Applied Physics*, 99 (2006) pp. 084909-1-084909-7.
P. Galliker et al., "Direct printing of nanostructures by electrostatic autofocussing of ink nanodroplets," *Nature Communications* 3, 890 (2012) pp. 1-9.

\* cited by examiner

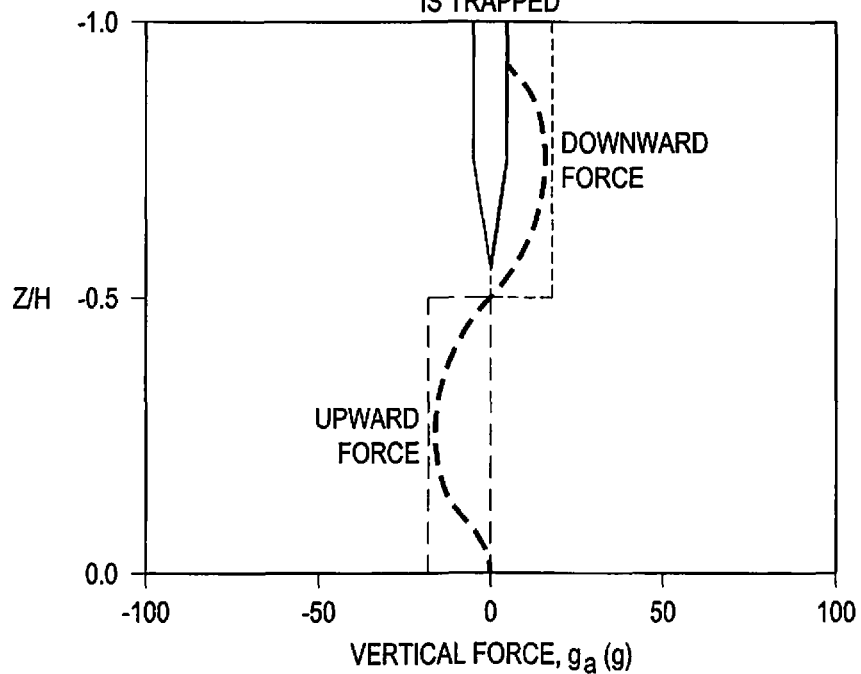
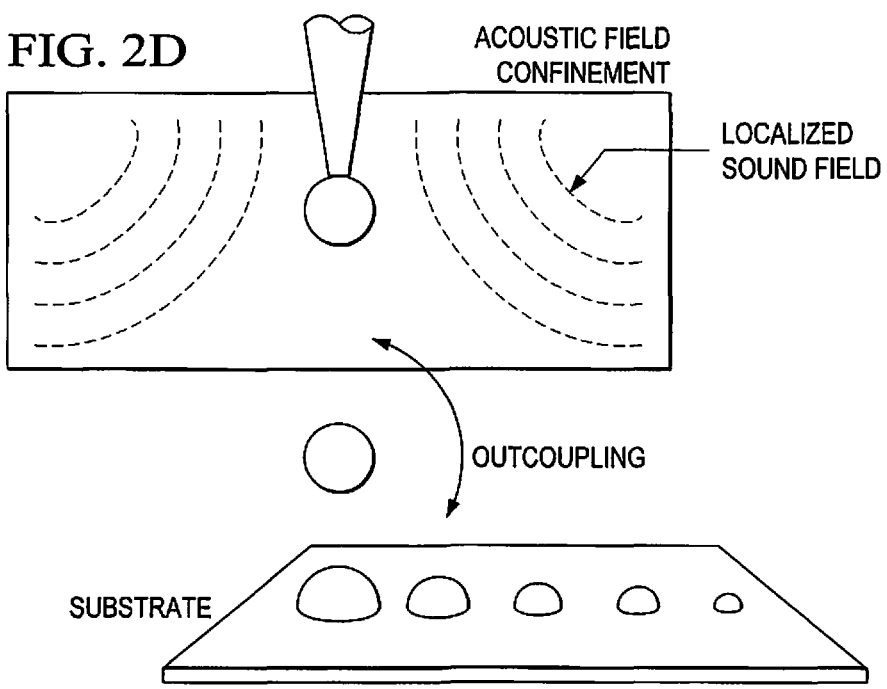

APPARATUS AND METHOD FOR ACOUSTOPHORETIC PRINTING

RELATED APPLICATIONS

The present patent document is the national stage of International Patent Application No. PCT/US2017/043539, which was filed on Jul. 24, 2017, and which claims the benefit of priority under 35 U.S.C. § 119(e) to U.S. Provisional Patent Application Ser. No. 62/367,318, which was filed on Jul. 27, 2016. Both of the aforementioned patent applications are hereby incorporated by reference in their entirety.

FEDERALLY SPONSORED RESEARCH OR DEVELOPMENT

This invention was made with government support under contract number DMR-1420570 awarded by the National Science Foundation. The government has certain rights in the invention.

TECHNICAL FIELD

The present disclosure is related generally to droplet generation 2D and 3D printing technology and more specifically to acoustophoretic printing.

BACKGROUND

Due to the limitations of state-of-the-art 2D and 3D printing methods, inks are often engineered to have physical properties satisfying the requirements of existing printers. A typical approach to rendering materials printable is to use additives to adjust the rheological properties of the ink. While enhancing printability, such additives may act as impurities in or otherwise prove detrimental to the printed structure.

In the realm of droplet-based printing techniques, inkjet technology represents a standard in industry and research. Despite its wide usage, only a narrow window of materials having a suitable combination of properties (e.g., viscosity and surface tension) may be successfully ejected from an ink jet printhead. This limitation can be attributed to the droplet detachment mechanism, which is based on the Rayleigh-Plateau instability. In inkjet technologies, a substantial mechanical excitation of the ink may be required in order to break the meniscus and eject a defined volume of liquid. Such a dynamic process implies a strong coupling between interfacial and viscous forces. From a physical point of view, the droplet generation of a defined ink can be characterized by a non-dimensional number, the Ohnesorge number Oh, and its inverse $Z=Oh^{-1}=(\rho\sigma 2R)^{1/2}/\mu$, with R being the characteristic length of the droplet, $\rho$ the density of the liquid, $\sigma$ its surface tension, and $\mu$ its viscosity of the ink. Unsurprisingly, the scientific literature reports that successful printing requires that the physical properties of the ink produce a Z value in a narrow window (1<Z<10).

Many inks of practical interest are based upon colloids or polymers that have relatively high viscosity and require dilution with additives for successful printing. Truly decoupling the dependence of the printing process from the physical properties of the ink may allow unprecedented freedom in the type and complexity of materials that can be 2D- and 3D-printed. A description of preliminary work to solve this problem may be found in Foresti et al., "Acoustophoretic Printing Apparatus and Method," International Publication No. WO 2015/110600, which is hereby incorporated by reference in its entirety.

BRIEF SUMMARY

An apparatus for acoustophoretic printing comprises: an acoustic chamber fully or partially enclosed by sound-reflecting walls for transmission of an acoustic field; an emitter at a first end of the acoustic chamber for generating the acoustic field; a chamber outlet at a second end of the acoustic chamber for locally enhancing the acoustic field and transmitting the acoustic field out of the acoustic chamber; and a nozzle in the acoustic chamber having a nozzle opening projecting into the chamber outlet for delivery of an ink into a high-intensity acoustic field and out of the acoustic chamber.

A method of acoustophoretic printing comprises generating an acoustic field at a first end of an acoustic chamber fully or partially enclosed by sound-reflecting walls. The acoustic field interacts with the sound-reflecting walls and travels through the acoustic chamber. The acoustic field is enhanced in a chamber outlet at a second end of the acoustic chamber. An ink is delivered into a nozzle positioned within the acoustic chamber. The nozzle has a nozzle opening projecting into the chamber outlet. The ink travels through the nozzle and is exposed to the enhanced acoustic field at the nozzle opening, and a predetermined volume of the ink is ejected from the nozzle opening and out of the acoustic chamber.

BRIEF DESCRIPTION OF THE DRAWINGS

FIG. 2C shows a plot of Z/H versus $g_a$ for the classical levitator.

FIG. 2D is a schematic showing localization of the acoustic field to permit outcoupling and printing of a detached droplet.

FIG. 7A shows a straight cylindrical geometry, and FIGS. 7B and 7C show modified cylindrical geometries having a nonzero radius of curvature at the subWAVE exit.

DETAILED DESCRIPTION

Acoustophoretic printing is an innovative approach for 2D- and 3D printing and may have application in a wide range of fields. The technology exploits the nonlinear effects of a subwavelength ultrasonic cavity to control droplet detachment from a nozzle by harnessing acoustic radiation pressure acting on the droplet. By exploiting Fabry-Perot acoustic resonances, as explained below, it may be possible to: (1) generate an acoustic field that intrinsically outcouples the detached drop; 2) create a highly localized acoustic field, which decouples the force from an underlying substrate; and 3) enhance the acoustic force magnitude by more than one or two orders of magnitude compared to existing systems. Advantages of the acoustophoretic printing approach described in this disclosure may include: 1) independence from any electromagnetic/optical properties or composition of the ink; 2) ink-viscosity independence; and 3) coverage of a droplet volume range exceeding two orders of magnitude with a single nozzle size.

Figure 1:
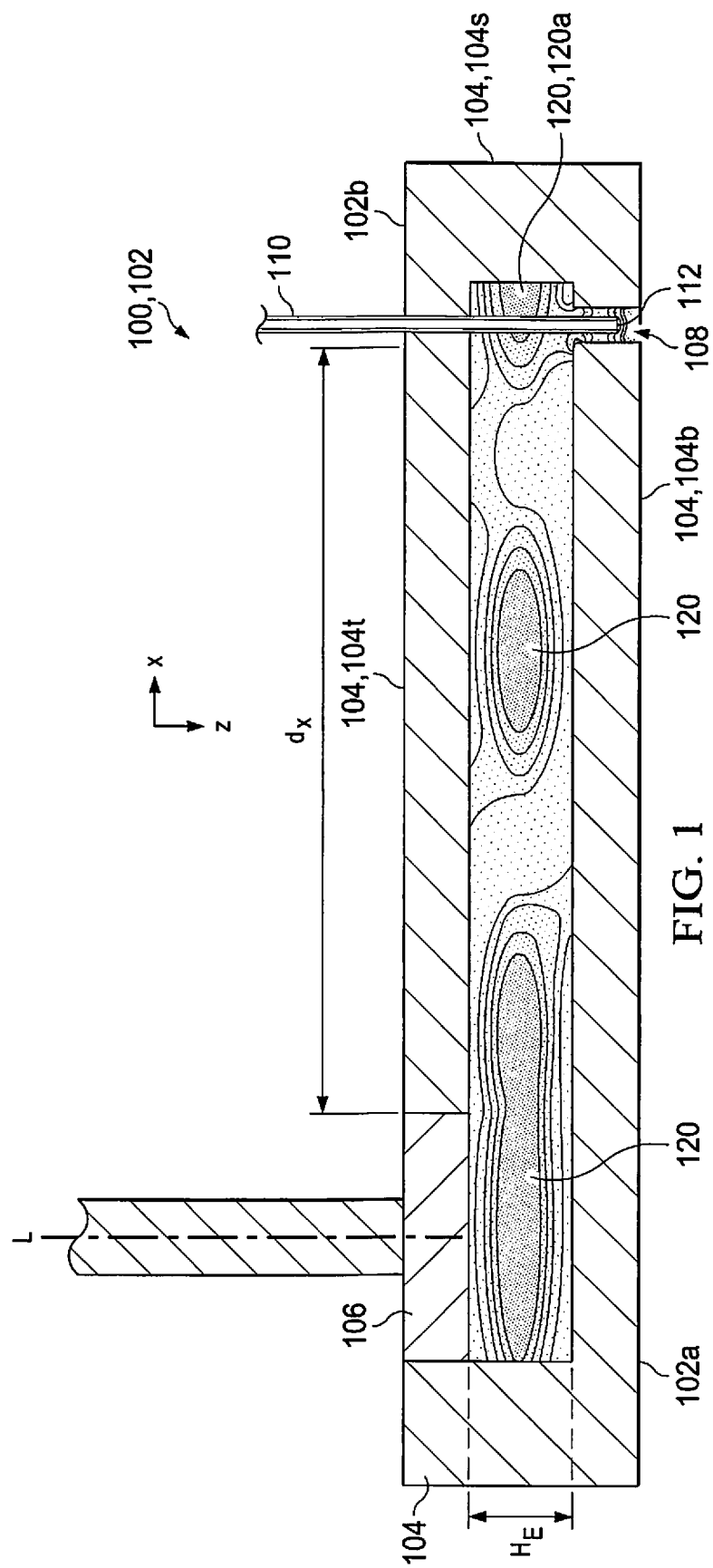
FIG. 1 is a schematic of an exemplary apparatus for acoustophoretic printing. The contour plot shows a finite element method (FEM) simulation of root-mean-square acoustic velocity $v_{rms}$ in the exemplary apparatus.

Referring to FIG. 1, an apparatus 100 for acoustophoretic printing includes an acoustic chamber 102 fully or partially enclosed by sound-reflecting walls 104 for transmission of an acoustic field with the chamber 102. An emitter 106 is positioned at a first end 102a of the acoustic chamber 102 for generating the acoustic field, and a chamber outlet 108 is positioned at a second end 102b of the acoustic chamber 102 for transmitting the acoustic field out of the chamber 102. The chamber outlet 108 is configured to locally enhance the acoustic field, as explained below, and may thus be referred to as a subWavelength Acoustophoretic Voxel Ejector (or "subWAVE"). The chamber outlet 108 is spaced apart from the acoustic emitter 106 by a distance $d_x$ in a direction normal to a longitudinal axis L of the emitter 106, where L may be understood to be aligned with the z-direction and $d_x$ may extend along the x-direction. A nozzle 110 in the acoustic chamber 102 has a nozzle opening 112 projecting into the chamber outlet 108 for delivery of an ink into the locally-enhanced acoustic field. Thus, ink droplets of very small volumes may be detached from the nozzle opening 112 and may exit the acoustic chamber 102. A substrate 116 may be positioned outside the acoustic chamber 102 and facing the chamber outlet 108 to receive the ejected ink. The substrate 116 may be moving relative to the nozzle opening 112 in an x-, y-, and/or z-direction such that the ink droplets are deposited in a predetermined 2D or 3D pattern on the substrate 116. Suitable inks may include both Newtonian and non-Newtonian fluids, viscoelastic fluids, yield stress fluids, polymer solutions, hydrogels, colloids, emulsions and complex fluids in general with Z values spanning a wide range (e.g., $0.001 \leq Z \leq 1000$). The substrate 116 that receives the ink droplets may comprise a solid, liquid or gel.

As shown in FIG. 1, the chamber outlet 108 may be a through-thickness cavity in one of the sound-reflecting walls of the acoustic chamber. The chamber outlet or subWAVE

108 is configured to achieve a resonant condition that strongly enhances the acoustic field and provides an acoustic force for droplet detachment. Microscale droplets having a diameter less than about 2 mm (or a volume less than about 4 mm$^3$) may be detached. At higher acoustic fields, smaller-size droplets (e.g., droplets having a diameter less than about 200 microns or a volume less than about 0.004 mm$^3$) may be detached. In some cases, droplets having a diameter as small as about 120 microns, or even as small as about 50 microns, may be detached. A lower bound for the droplet diameter may be about 10 microns. Generally speaking, the subWAVE can be configured to allow detachment of droplets having diameters in a range from about 10 microns to about 2 mm, where a diameter range of 50 microns to 2 mm, or 200 microns to 2 mm, is more typical. The chamber outlet or subWAVE 108 may exhibit an extraordinary acoustic field enhancement based on the Fabry-Perot cavity principle.

Figure 3A:
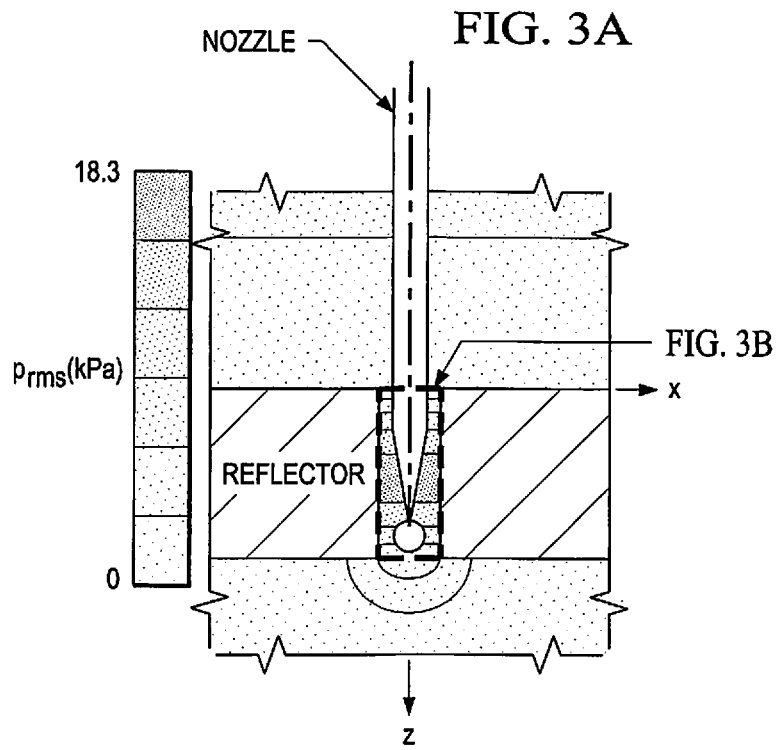
FIG. 3A shows a FEM simulation of root-mean-square acoustic pressure $p_{rms}$ in an exemplary subWavelength Acoustophoretic Voxel Ejector ("subWAVE").
Figure 3B:
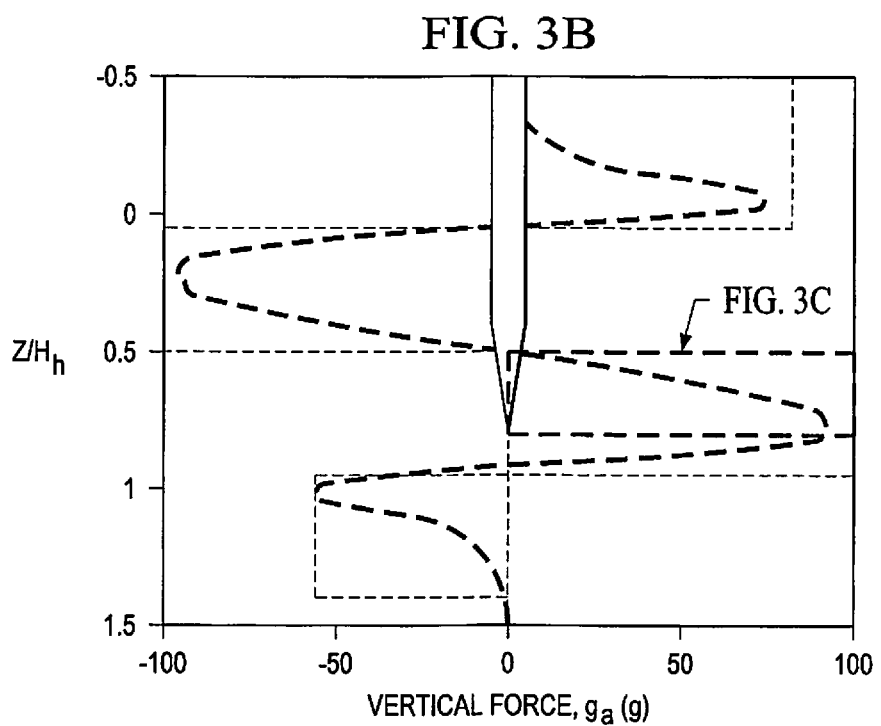
FIG. 3B shows a plot of $Z/H_h$ versus $g_a$ for the exemplary subWAVE.
Figure 3C:
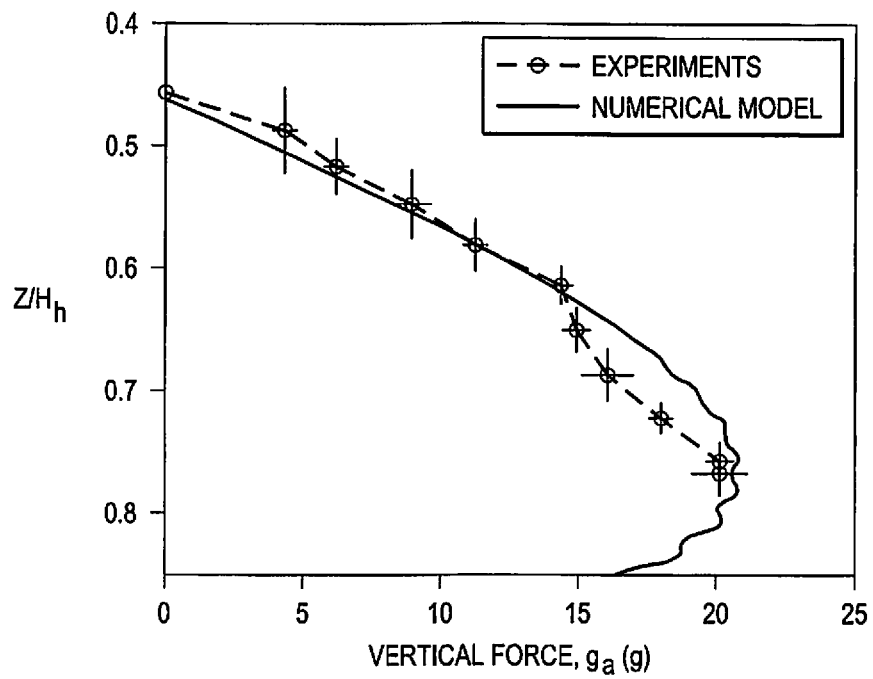
FIG. 3C shows that experimental data are consistent with the numerically predicted force distribution inside the subWAVE as a function of the z-coordinate.
Figure 3D:
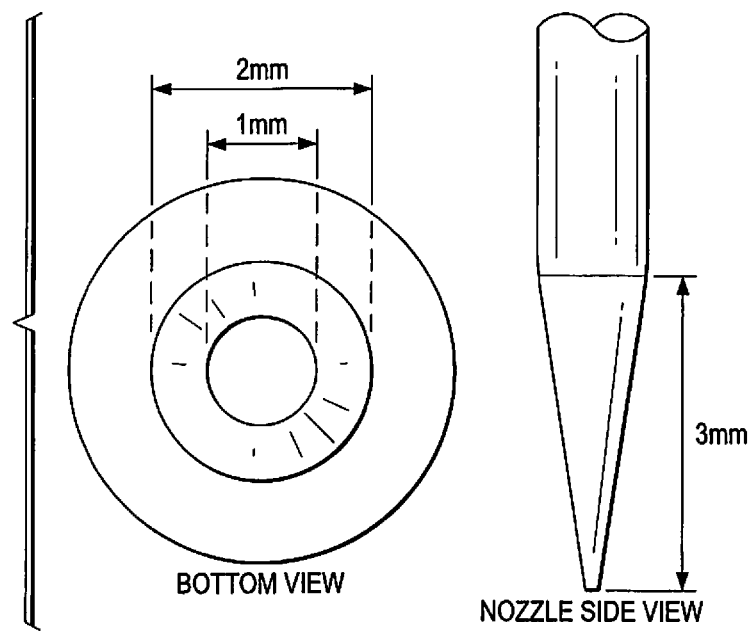
FIG. 3D includes photographs of an exemplary nozzle inside a chamber outlet (subWAVE) as seen from a bottom view and also from a side view.
Figure 3E:
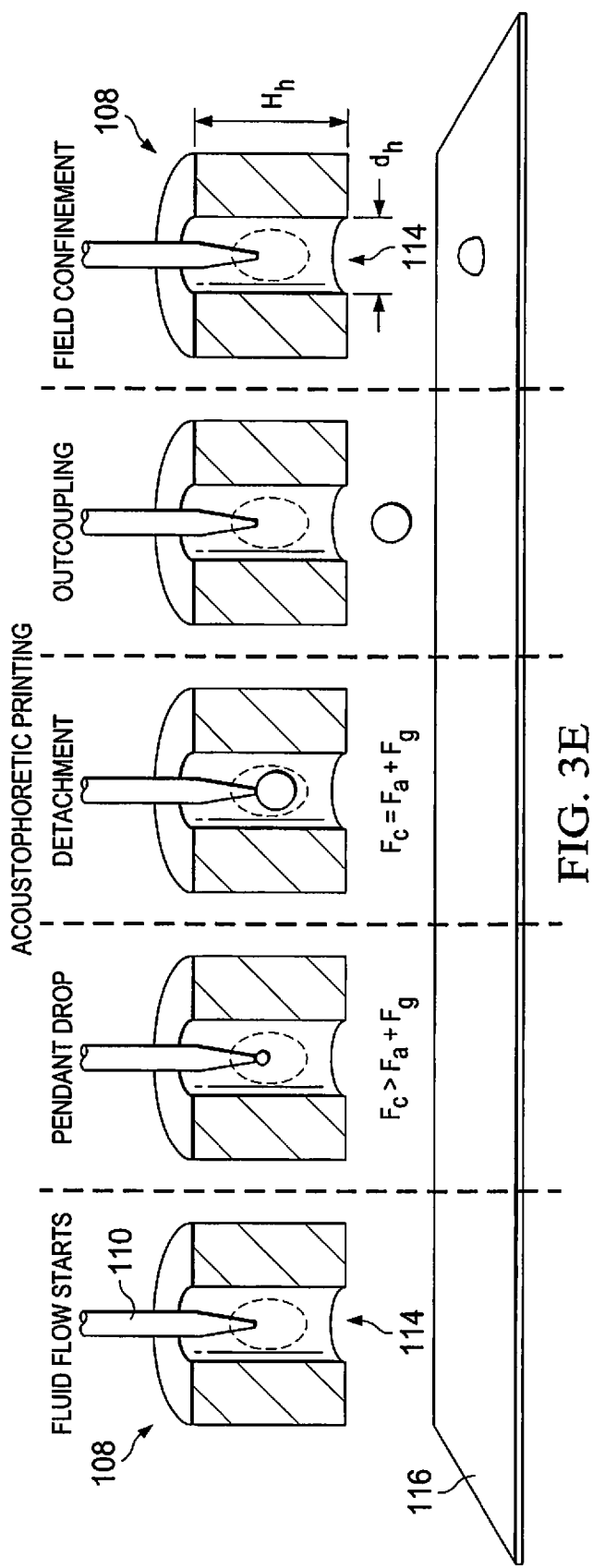
FIG. 3E is a schematic showing outcoupling and printing of a droplet from a cylindrical subWAVE of dimensions $d_h$ and $H_h$.

The chamber outlet 108 may have a width or diameter $d_h$ and a height $H_h$, as indicated in FIG. 3E, where $d_h$ and $H_h$ may be defined in terms of the wavelength $\lambda$ of the acoustic field. To achieve a resonant condition, $d_h$ and $H_h$ may fall within the following ranges: $0.01\lambda \leq d_h \leq 0.20\lambda$ and $0.30\lambda \leq H_h \leq 0.60\lambda$ or $0.80\lambda \leq H_h \leq 1.0\lambda$, according to the related Fabry-Perot resonance. Since the Fabry-Perot resonator may have any cross section (e.g., cylindrical, square— as reported in FIG. 4A—or polygonal, ellipsoidal, irregular, etc.), it is more convenient to refer to its cross-sectional area A. So to achieve a resonant condition, A and $H_h$ may fall within the following range: $\pi/4 \cdot (0.01)^2/\lambda^2 \leq A \leq \pi/4 \cdot (0.2)^2/\lambda^2$, and $0.30\lambda \leq H_h \leq 0.60\lambda$ or $0.80\lambda \leq H_h \leq 1.0\lambda$, according to the related Fabry-Perot resonance. Typically, the wavelength $\lambda$ of the acoustic field in air is about 1.4 mm for a system operating at an acoustic frequency of about 250 kHz, and thus, for some embodiments, 14 microns $\leq d_h \leq$ 280 microns, corresponding to 616 $\mu m^2 < A < 0.2463$ mm$^2$, and 420 microns $\leq H_h \leq$ 840 microns or 1120 microns $\leq H_h \leq$ 1400 microns. For use at higher frequencies and longer wavelengths, the dimensions of the subWAVE may be increased. For example, for a wavelength $\lambda$ of about 14 mm, $d_h$ and $H_h$ may fall within the following ranges: 0.14 mm $\leq d_h \leq$ 2.8 mm, corresponding to 0.0616 mm$^2 < A < 24.63$ mm$^2$, and 4.2 mm $\leq H_h \leq$ 8.4 mm or 11.2 mm $\leq H_h \leq$ 14.0 mm. More generally speaking, considering a range of possible wavelengths, 14 microns $\leq d_h \leq$ 2.8 mm, corresponding to 616 $\mu m^2 < A < 24.63$ mm$^2$, and 420 microns $\leq H_h \leq$ 14.0 mm.

Figure 2A:
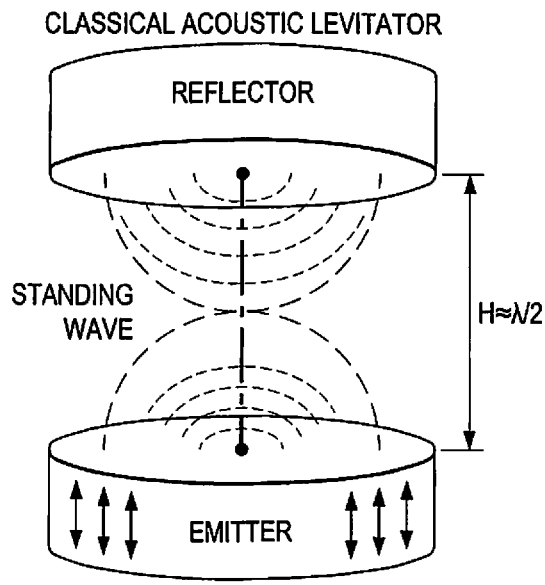
FIG. 2A shows a classical acoustic levitator, where a detached droplet may be trapped in the acoustic field, and outcoupling is not possible.
Figure 2B:
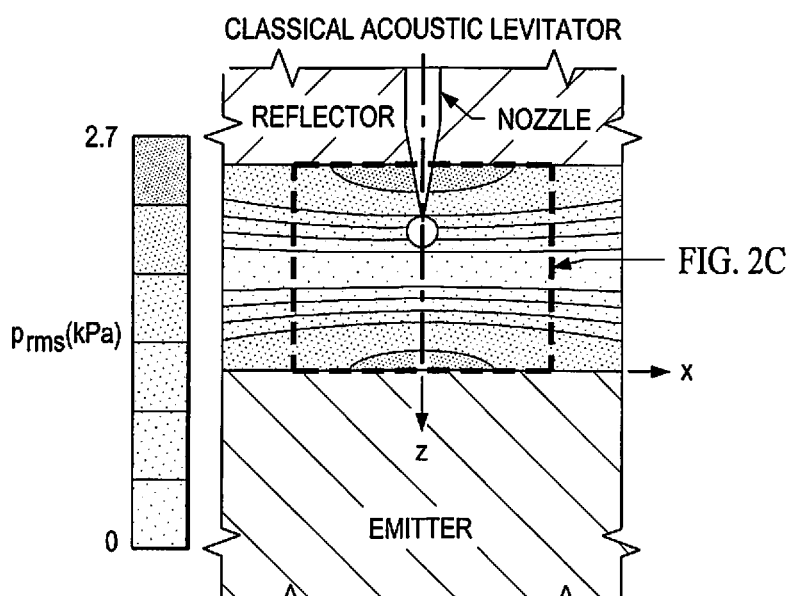
FIG. 2B shows a FEM simulation of root-mean-square acoustic pressure $p_{rms}$ in the classical acoustic levitator of FIG. 2A.

The achievement of a resonant condition in the chamber outlet or subWAVE 108 may be exhibited by an enhancement in acoustic pressure. FIGS. 2B and 3A show FEM simulations of root-mean-square acoustic pressure $p_{rms}$ in a classical acoustic levitator (FIG. 2A) and in an exemplary subWAVE (FIG. 3E), respectively. In the classical levitator, an acoustic standing wave generated between an emitter or oscillating source and a reflector may have a resonant condition, where a distance H between the oscillating source and the reflector is a multiple of half of the acoustic wavelength $\lambda$. For example, when $H \approx \lambda/2$, a pressure node is generated between the emitter and reflector, and the acoustic field can push small samples ($R < \lambda/2$) towards the center at about $H \approx \lambda/4$. In the plot of Z/H versus $g_a$ in FIG. 2B, H represents the distance H between the oscillating source and reflector and $g_a$ represents the acoustic acceleration.

Referring now to FIGS. 3A and 3E, the $p_{rms}$ in the chamber outlet is approximately eight times higher than in the classical acoustic levitator, showing evidence of resonance and leading to nearly two orders of magnitude enhancement in acoustophoretic forces, as shown in FIG. 3B. $H_h$ refers to the height or length of the chamber outlet 108, as illustrated in FIG. 3E. The chart of FIG. 3B reveals that downward forces act on the nozzle opening 112 in the chamber outlet 108, and FIG. 3C shows experimental data that confirm the numerically predicted force distribution inside the chamber outlet 108 as a function of the z-coordinate. FIG. 3D includes schematics of an exemplary nozzle 110 inside an exemplary chamber outlet 108 as seen from a bottom view and also from a side view. It should be noted that, while the figures show the chamber outlet 108 as having a longitudinal axis oriented along the z-direction or the vertical direction as defined by gravity, such an orientation is not required. Since the acoustic force may be greater than the force of gravity, ink may be ejected from the acoustic chamber even with a non-vertical (e.g., horizontal) orientation of the nozzle 110 and the chamber outlet 108.

Figure 3F:
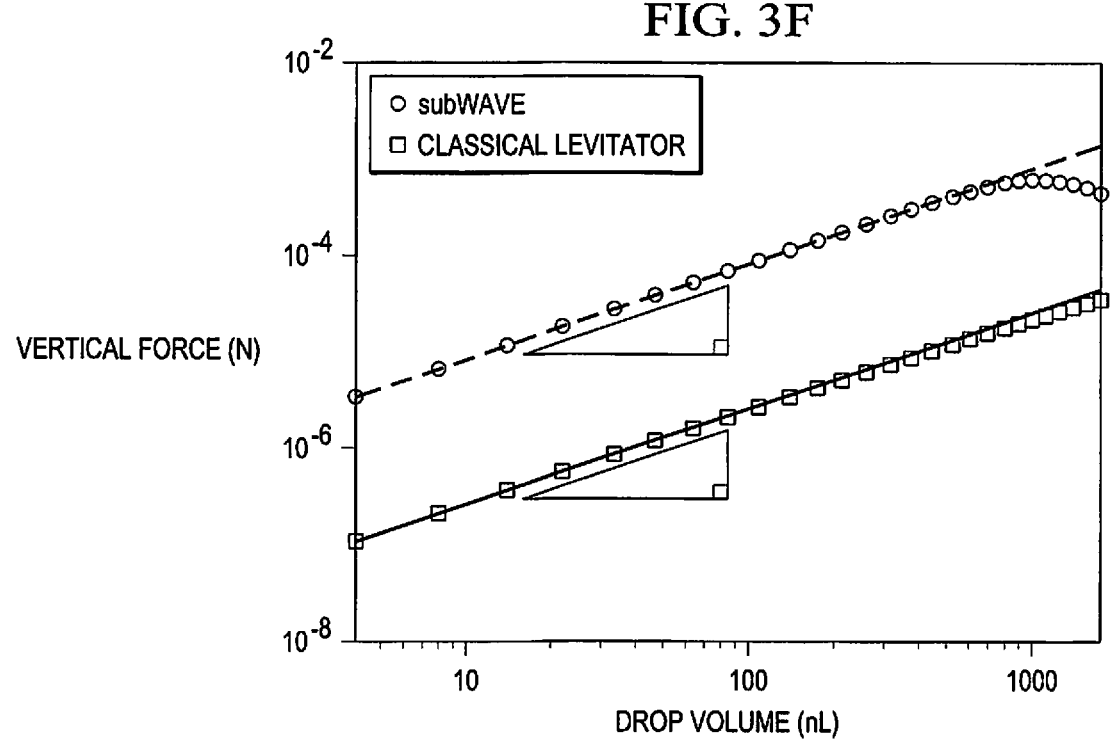
FIG. 3F shows a comparison of the acoustic forces generated by the exemplary subWAVE and a classical levitator as a function of drop volume.

In contrast to traditional standing wave levitators, the subWAVE 108 allows for ejection of the detached droplet from the acoustic chamber 102, as shown schematically in FIG. 3E for an exemplary cylindrical subWAVE 108 of dimensions $d_h$ and $H_h$. This unique characteristic is the result of the double open-ended nature of the chamber outlet 108 along the central z-axis, and by the designed axial force gradient, which allows the detached droplet to be ejected. In addition to such qualitative features, in the subWAVE 108 the acoustic force is enhanced up to two orders of magnitudes compared to the typical levitator configuration, allowing for forces exceeding 100 gV$\rho$ and therefore detachment and ejection of subnanoliter volumes of ink. Acoustic resonance leads to high acoustic pressure amplification while the subWAVE 108 keeps the field strongly confined. Once the total acoustophoretic and gravitational forces $F_a$, $F_g$ exceed the capillary force $F_c$, as illustrated in FIG. 3E, the droplet may be detached and outcoupled from the chamber exit 114 of the subWAVE 108. A comparison of the acoustic forces generated by the subWAVE 108 compared to a classical levitator is shown in FIG. 3F as a function of drop volume.

Since acoustophoretic printing can generate acoustic forces ($F_a$) more than two order of magnitude higher than the gravitational force ($F_g$), the ballistic trajectory of the ejected droplet allows for accurate printing even in a direction orthogonal to the force of gravity, as mentioned above. Indeed, for a substrate 116 positioned within 1-3 mm from the chamber outlet 108, gravitational effects on the droplet trajectory are minimal. Experiments in which an ink comprising a water-glycerol mixture (50%) is ejected from a chamber outlet 108 along a trajectory orthogonal to the direction of gravity show that, when $F_a > 10 F_g$, the trajectory is poorly influenced by the gravitational force up to several millimeters from the nozzle opening 112. Since the subWAVE 108 need not be oriented such that ejection of the droplet occurs in the vertical (downward) direction, as defined by the force of gravity, the term "vertical force" used herein may be understood to refer more generally to an acoustic ejection force that may act in a vertical or other direction to expel the droplet from the exit 114 of the subWAVE 108.

Figure 4A:
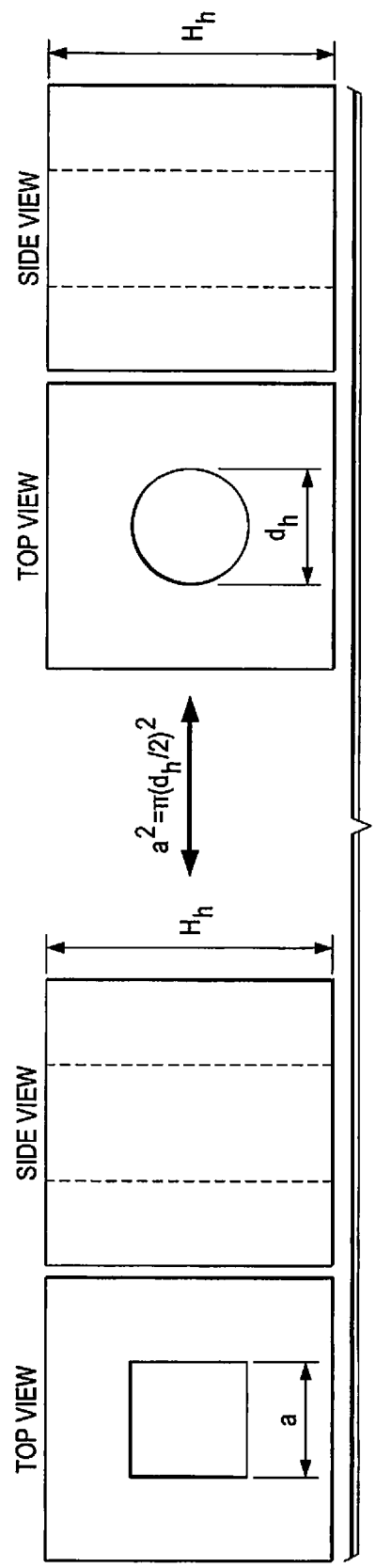
FIG. 4A shows an exemplary Fabry-Perot resonator based on a square cavity and an equivalent resonator with a circular cross-section.
Figure 4B:
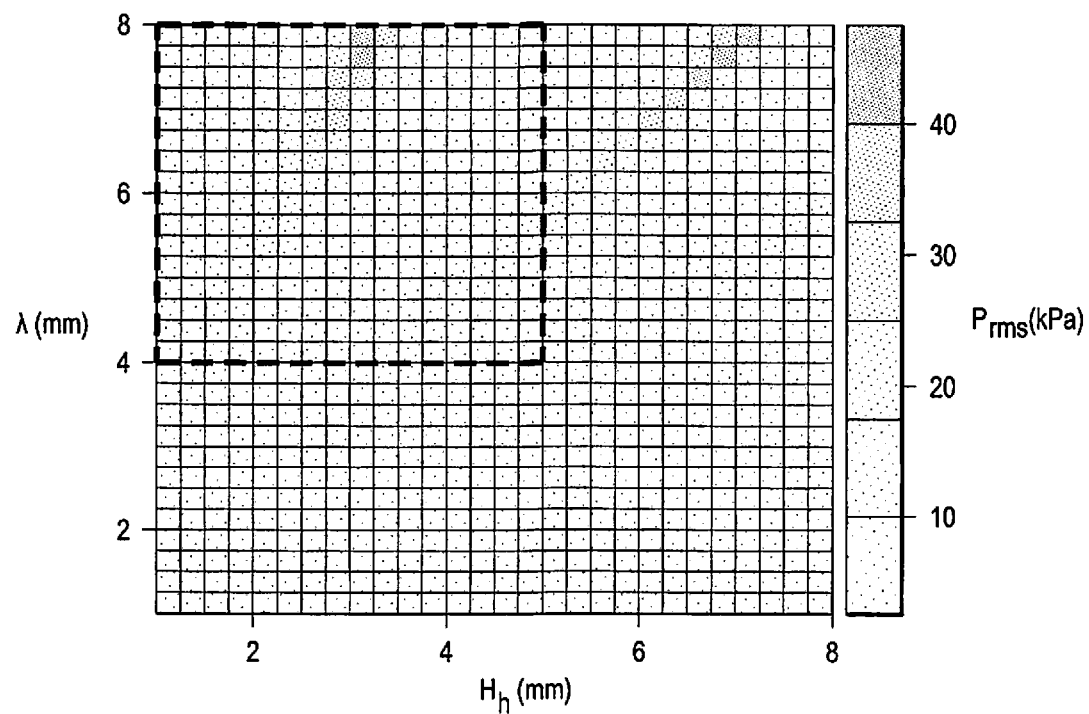
FIG. 4B shows validation of a numerical model employed to calculate the acoustic field inside the subWAVE using results of Christensen et al., *Phys. Rev. Lett.*, 101 (2008) for the (square) Fabry-Perot resonator of FIG. 4A, where the peak of the $P_{rms}$ within the cavity is reported.
Figure 4C:
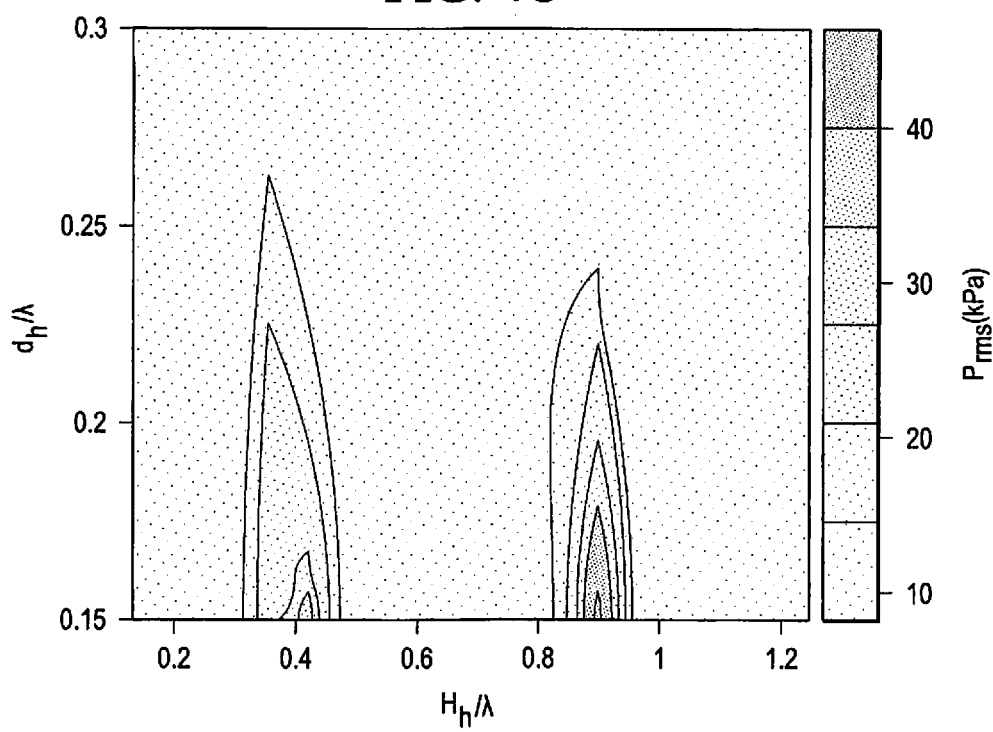
FIG. 4C shows a $H_h$–$d_h$ parametric space, which is convenient to consider when optimizing the subWAVE for a fixed frequency.
Figure 4D:
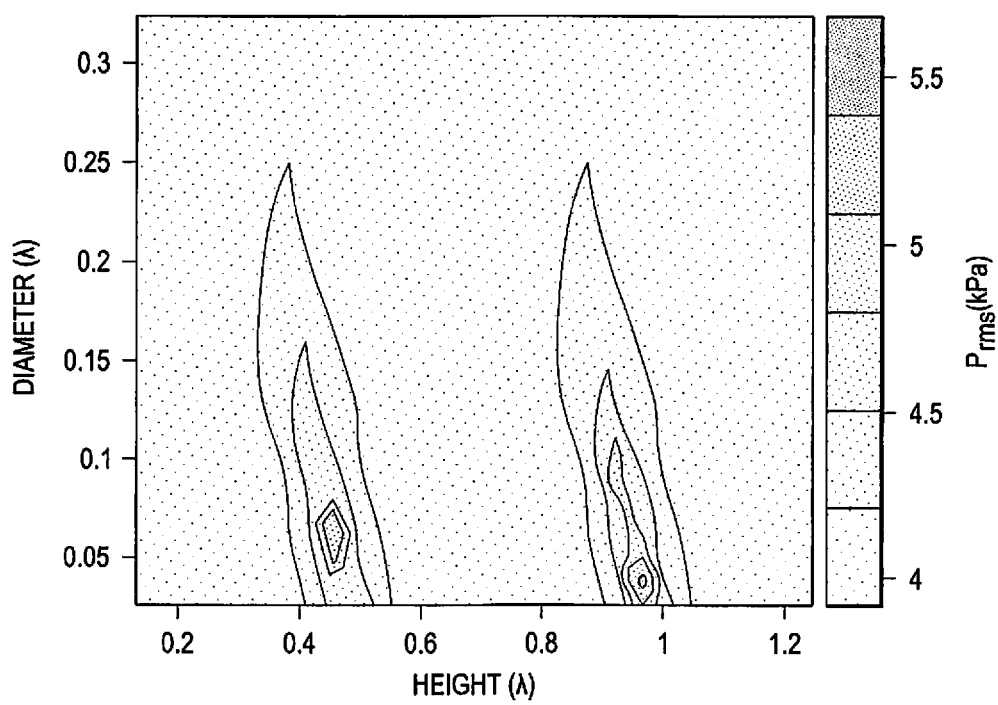
FIG. 4D shows a larger $H_h$–$d_h$ parametric space.

Fabry-Perot resonance may be understood to be a manifestation of constructive or destructive acoustic wave interference over a certain path length that can lead to multiple transmission peaks. In the present case, a subwavelength resonance is generated in the chamber outlet 108 (in addition to the primary standing wave in the acoustic chamber 102) may lead to an enhancement in the acoustic field. A small departure from the optimal dimensions of a Fabry-Perot resonator can strongly reduce the acoustic field and thus the vertical force inside the subWAVE 108. FIG. 4A shows an exemplary Fabry-Perot resonator based on a square cavity that was used in the work of Christensen et al., *Phys. Rev. Lett.*, 101 (2008). The square resonator can be converted to an equivalent resonator with a circular cross-section as shown. FIG. 4B shows validation of the numerical model employed herein based on the results of Christensen et al. In that work, the transmittance (normalized on the cavity cross-sectional area) was calculated, while in this investigation the peak of the $P_{rms}$ within the cavity is reported. To optimize the subWAVE for a fixed frequency, it is more convenient to consider a $H_h$–$d_h$ parametric space, as shown in FIG. 4C. A complete $H_h$–$d_h$ parametric space is shown in FIG. 4D. $H_h$=0.36λ and $d_h$=0.14λ are selected within the first Fabry-Perot resonance space.

The acoustic chamber 102 may include a sound-reflecting side wall 104s at the second end to facilitate formation of a velocity antinode 120a in the acoustic field adjacent to the chamber outlet 108. FIG. 1 provides an illustration of an exemplary root-mean-square velocity field in the acoustic chamber 102, where the red spots depict velocity antinodes 120, or regions of high velocity. Simulations and experiments show that the intensity of the acoustic field in the chamber outlet 108 depends on the proximity of the nearest velocity antinode 120a to the outlet 108. The closer the sound-reflecting side wall 104s is to the chamber outlet 108, the higher the acoustic field may be inside the chamber outlet 108. Ideally, the velocity antinode 120a is directly above the chamber outlet 108, as shown in FIG. 1. Additional chamber outlets can be added adjacent to (e.g., below) other velocity antinodes 120, thereby providing a chamber configuration suitable for use with multiple nozzles. The distance $d_x$ between the emitter 106 and the outlet 108 may be determined at least in part by the number of nozzles 110 to be incorporated into the acoustic chamber 102. At a minimum, the distance $d_x$ is large enough (e.g., at least about 1 mm) to accommodate at least one nozzle positioned adjacent to the emitter 106. Typically, the distance $d_x$ is at least about 10 mm, at least about 30 mm, or at least about 50 mm, and the distance $d_x$ may be as large as about 1 m or as large as about 500 mm.

Figure 5:
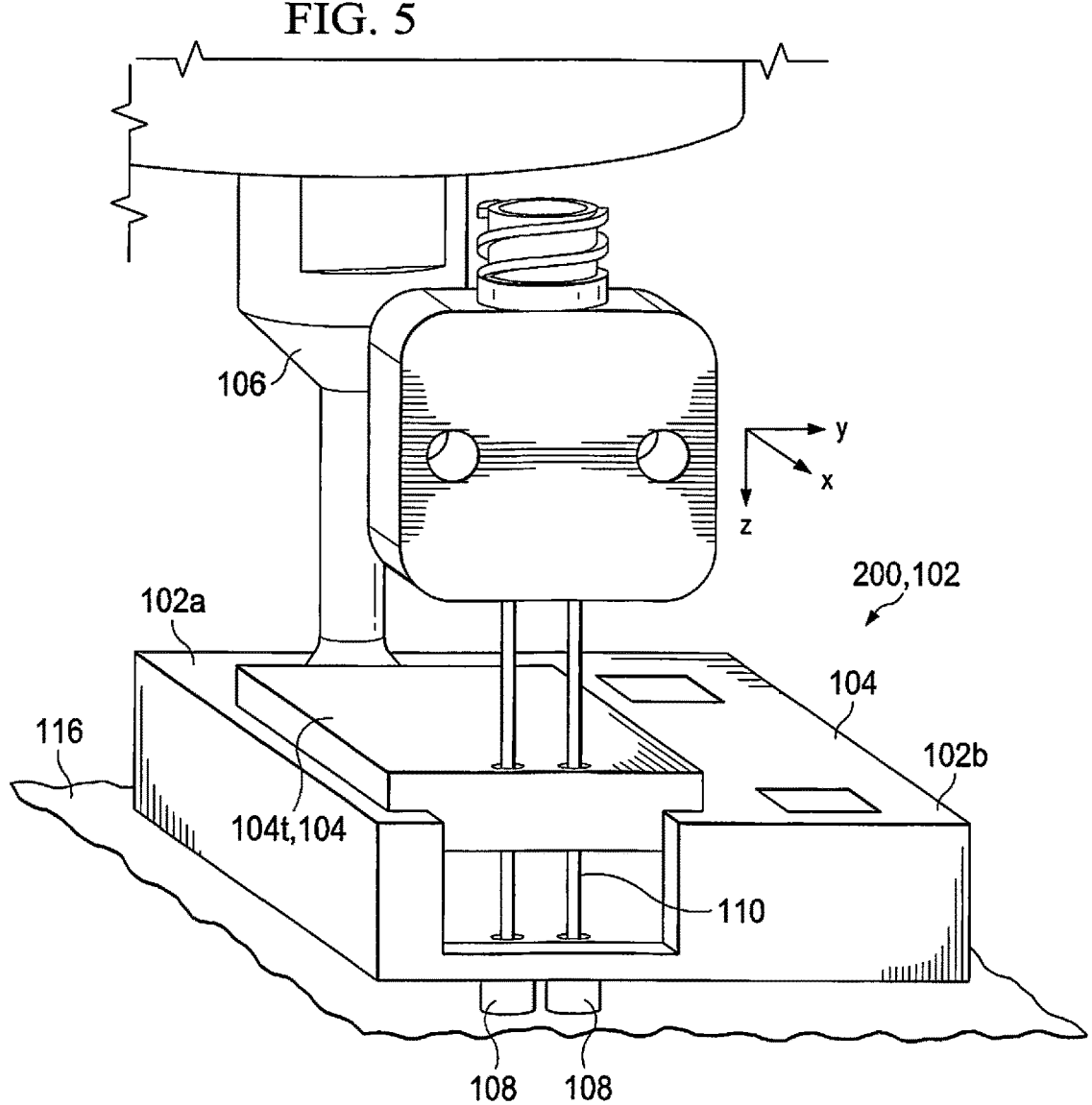
FIG. 5 shows another exemplary apparatus for acoustophoretic printing, which includes an acoustic chamber comprising two chamber outlets and two nozzles.

FIG. 5 shows another exemplary apparatus 200 for acoustophoretic printing. The acoustic chamber 102 includes a plurality of chamber outlets 108 and a plurality of nozzles 110, where each nozzle 110 has a nozzle opening 112 projecting into one of the chamber outlets 108. The nozzles 110 and the chamber outlets 108 may be spaced apart along an x-direction between the first and second ends 102a, 102b of the acoustic chamber 102. The nozzles 110 and the chamber outlets 108 may also or alternatively be spaced apart along a y-direction. Thus, a 2D arrangement of nozzles 110 may be included in the apparatus 200.

As indicated above, the acoustic chamber 102 may be partially or fully enclosed by the sound-reflecting walls 104. Advantageously, the acoustic chamber 102 includes at least two or at least three sound-reflecting walls and as many as six or more sound-reflecting walls. For example, the acoustic chamber 10 may include a sound-reflecting top wall 104t adjacent to the acoustic emitter 106 and a sound-reflecting bottom wall 104b in opposition to the acoustic emitter 106. The sound-reflecting walls may be formed of any of a number of solid materials, including metals, ceramics, polymers, natural fiber materials (e.g., wood, paper), plaster, and others. The acoustic chamber may have a rectangular parallelepiped shape, as shown for example in FIG. 5, or the chamber may have another elongated shape, such as a cylindrical shape. In such a case, the sound-reflecting top and bottom walls may be portions of a single curved surface. The acoustic emitter 106 may comprise a piezoelectric transducer, a mechanical oscillator, a magnetostrictive oscillator or another source of sound waves. The longitudinal axis of the emitter may be defined by the direction of the oscillations.

The acoustic field generated in the acoustic chamber 102 may be highly dependent on the dimensions of the chamber 102, including the distance $d_x$ between the emitter 106 and the chamber outlet 108, the height of the emitter 106 (emitter height $H_E$), the height of the sound-reflecting top wall 104t (reflector height $H_R$), and the distance $d_{wall}$ between the chamber outlet 108 and the sound-reflecting side wall 104s. The distance $d_{wall}$ is shown schematically in FIGS. 6A and 6B, and the emitter and reflector heights $H_E$, $H_R$ are labeled in FIG. 14. The emitter and reflector heights $H_E$, $H_R$ can strongly influence the shape and intensity of the acoustic field and can affect the position of velocity and pressure antinodes. The smaller $d_{wall}$ is, the higher the intensity of the acoustic field is in the chamber outlet 108. The determination of optimal values of $H_R$ and $H_E$ is discussed below. Typically, $H_R$ may lie in the range from about 0.3λ to about 0.7λ, $H_E$ may lie in the range from about 0.3λ to about 0.7λ, $d_{wall}$ may lie in the range from about 0.0λ to about 0.3λ, and $d_x$ may be from about 1 mm to about 500 mm. Varying these dimensions may serve as a tool for adjusting and selecting the size of the ejected droplets, as discussed below in the section "Experimental and Computational Details."

The acoustic chamber may include a fluid medium, i.e., a gas or liquid such as ambient air, water or oil, which can transmit sound waves. The acoustic chamber may be immersed in the fluid medium. In some cases, the fluid medium may be forced through the acoustic chamber at a constant or variable flow rate.

The nozzle 110 may take the form of a glass pipette or other fluid conduit that has a length sufficient to pass through the interior of the acoustic chamber 102 and into the chamber outlet 108. The nozzle 110 may include a nozzle opening 112 having a diameter in the range from about 1 micron to about 1 mm, and more typically from about 10 microns to about 100 microns. To prevent wetting of the nozzle during printing, the nozzle 110 may include a hydrophobic coating at or near the nozzle opening 112. Typically, the nozzle opening 112 is substantially centered within the chamber outlet (e.g., substantially aligned with a longitudinal axis of the chamber outlet) 108 as shown in FIG. 3D to promote ejection of a droplet having a straight trajectory. If the nozzle opening 112 is off-center, the ejected droplet may move off-axis along a tilted trajectory as it exits the chamber outlet. If desired, the trajectory of the ejected droplet may be controlled by changing the position of the nozzle opening 112 within the chamber outlet 108, as discussed in detail below. The nozzle 110 may be secured (e.g., by a Luer-Lock connector) to a syringe pump or other ink dispenser that is located outside of the acoustic chamber 102.

Figure 6A:
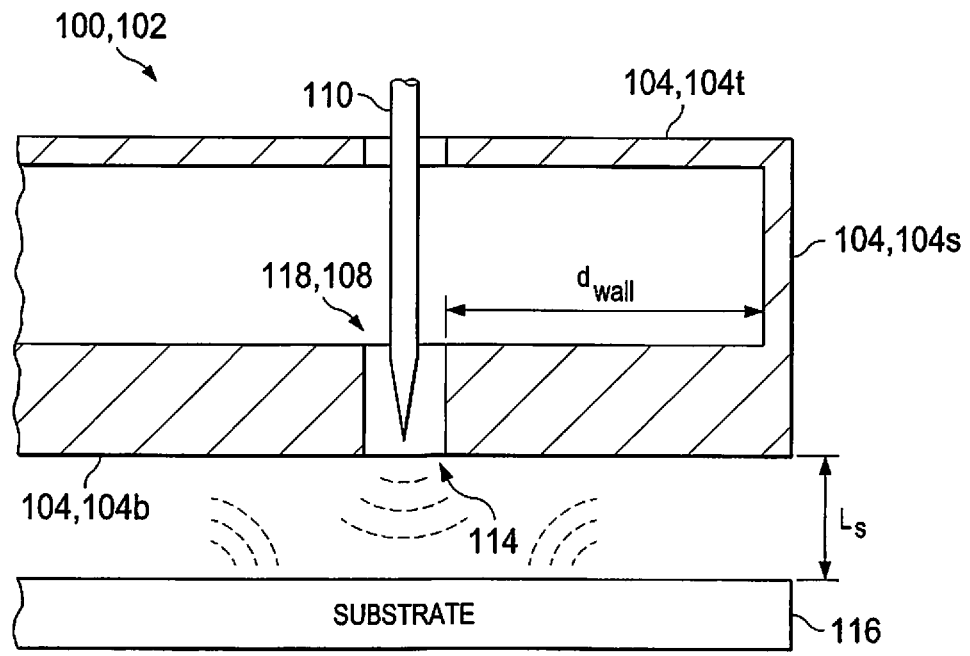
FIG. 6A shows a nozzle projecting into the chamber outlet at the second end of an exemplary acoustic chamber, and also a substrate positioned a distance $L_s$ away from the exit of the chamber outlet.
Figure 6B:
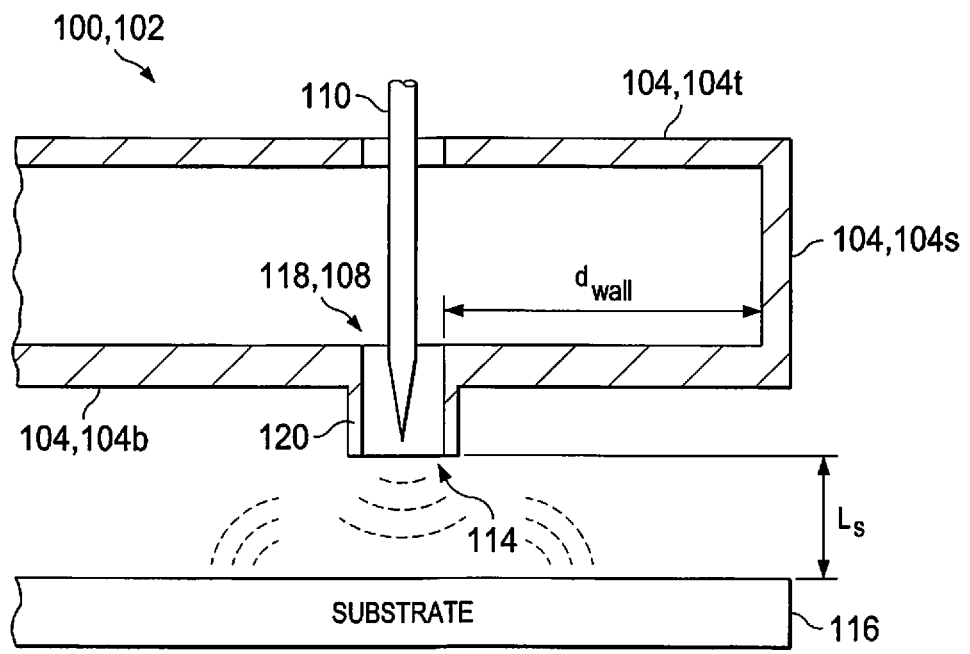
FIG. 6B shows a nozzle projecting into the chamber outlet at the second end of another exemplary acoustic chamber, where the chamber outlet includes an outlet portion extending beyond the sound-reflecting bottom wall, which has a reduced thickness compared to the sound-reflecting bottom wall shown in FIG. 6A.

As indicated above, the chamber outlet 108 may take the form of a through-thickness cavity 118 in one of the sound-reflecting walls 104 of the acoustic chamber 102. Referring to FIGS. 6A and 6B, the sound-reflecting wall 104 containing the through-thickness cavity 118 may be a sound-reflecting bottom wall 104b. As shown in FIG. 6B, the through-thickness cavity 118 may further include an outlet portion 120 extending beyond the sound-reflecting bottom wall 104b, which has a reduced thickness compared to the sound-reflecting bottom wall 104b shown in FIG. 6A. The outlet portion 120 may have a wall thickness less than that of the sound-reflecting bottom wall 104b, which may have some advantages, including allowing for a reduced distance $L_s$ between the subWAVE exit or opening 114 and the substrate 116, as discussed in the Examples. For example, the distance $L_s$ may be as small as $0.1\lambda$ in the configuration of FIG. 6B.

Figure 7A:
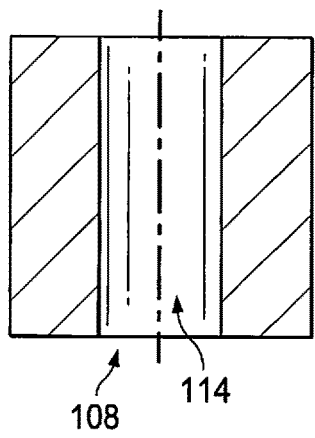
FIGS. 7A-7C are cross-sectional schematics showing possible geometries for the chamber outlet.
Figure 7B:
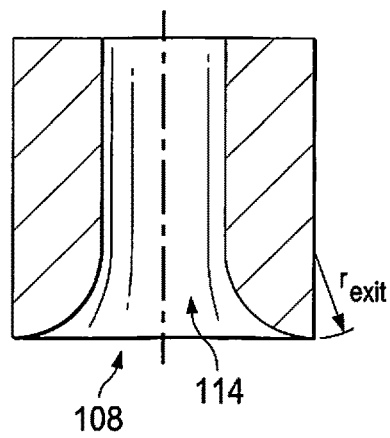
Figure 7C:
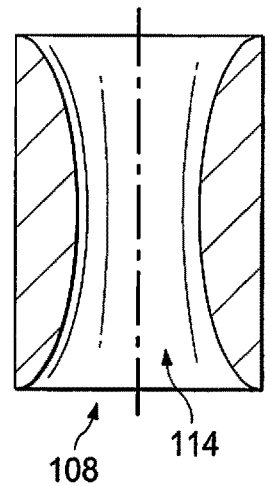

The chamber outlet 108 may have a cylindrical geometry, as shown by the image of FIG. 3D and the longitudinal cross-sectional schematic of FIG. 7A, or a modified cylindrical geometry, as shown for example by the longitudinal cross-sectional schematics of FIGS. 7B and 7C. In both of the modified cylindrical geometries shown in FIGS. 7B and 7C, the subWAVE exit or opening 114 has a nonzero radius of curvature (or exit radius) ($r_{exit}$). For example, the subWAVE exit 114 may have radius of curvature $r_{exit} > \frac{1}{20} d_h$. The geometry of FIG. 7B (which may be referred to as "smooth") has a much smaller radius of curvature than that of the geometry of FIG. 7C (which may be referred to as "convex"). It should be understood that the terms "cylindrical geometry" and "modified cylindrical geometry" are not intended to limit the chamber outlet 108 to a geometry having a circular transverse cross-section. For either the cylindrical or modified cylindrical geometry, a given transverse cross-section of the chamber outlet 108 may be circular, oval, square (as shown for example in FIG. 4A), pentagonal, hexagonal, or another symmetric or nonsymmetric shape.

Figure 8:
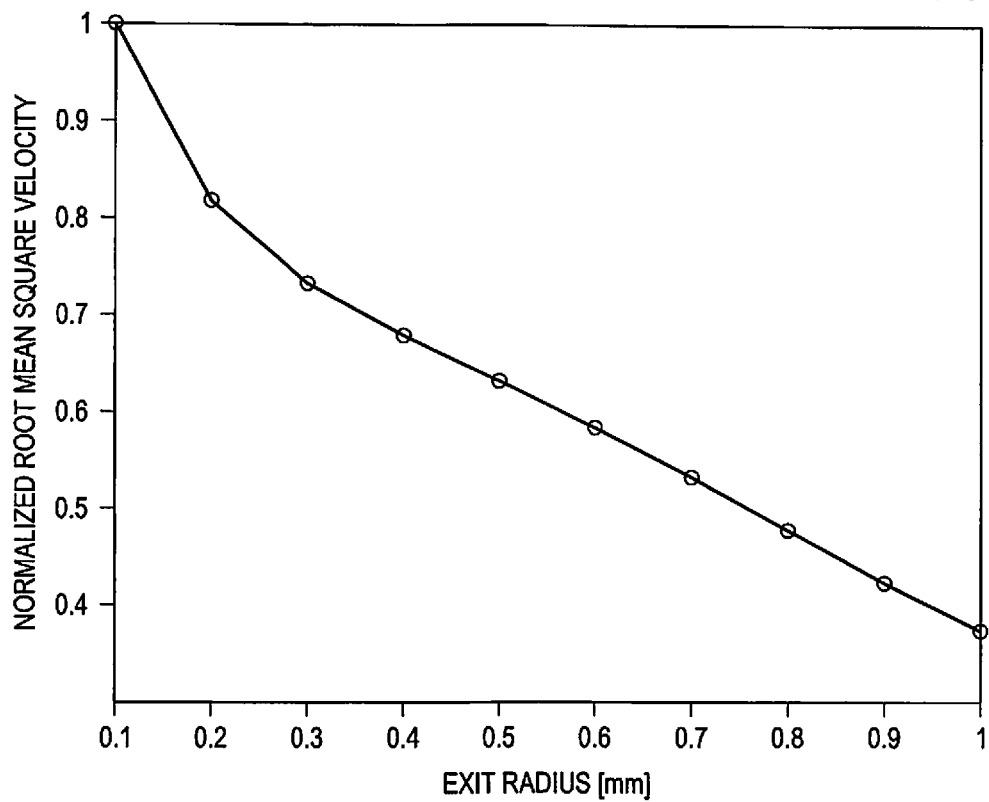
FIG. 8 shows the effect of the radius of curvature (or exit radius) of the subWAVE exit on the normalized root-mean-square velocity ($v_{rms}$).
Figure 9:
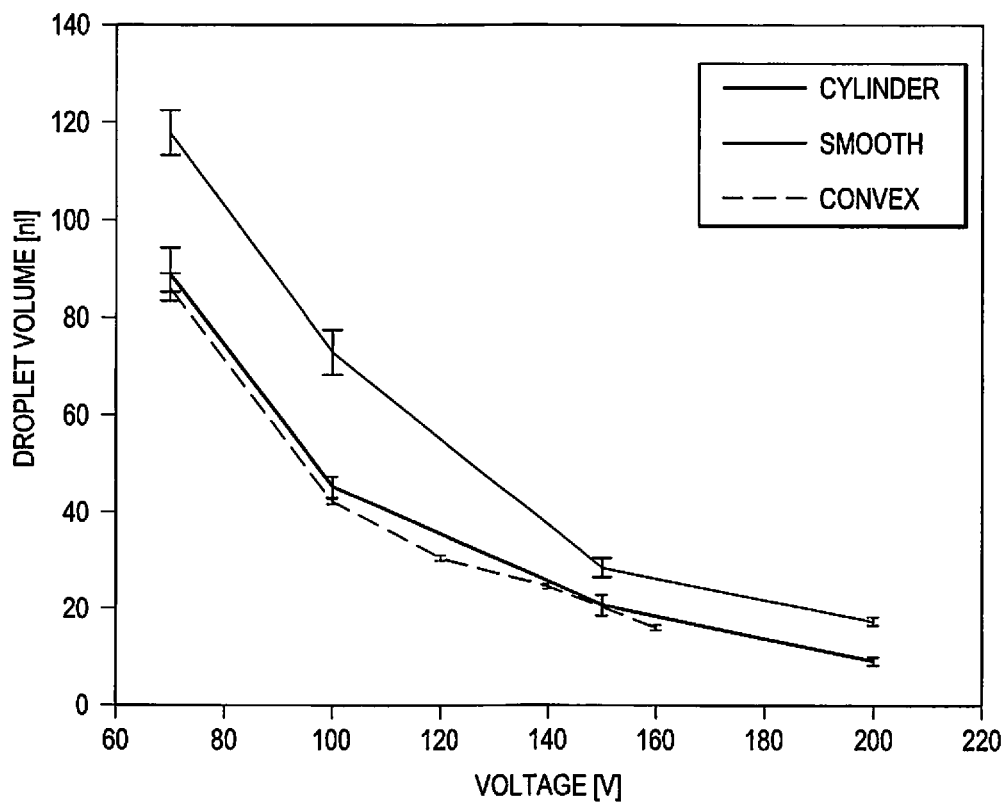
FIG. 9 shows the relationship between droplet volume and voltage for the subWAVE geometries of FIGS. 7A-7C.

FIG. 8 shows the effect of the radius of curvature of the subWAVE exit 114 on the normalized root-mean-square velocity ($v_{rms}$), as determined by simulations using a 2D axisymmetric model. The modeling data show that $v_{rms}$ decreases when the exit radius ($r_{exit}$) increases from 0.1 mm to 1 mm for $\lambda$=14 mm. FIG. 9 shows the relationship between droplet volume and the voltage applied to the emitter for the subWAVE geometries of FIGS. 7A-7C. The droplet size is determined by analyzing images of ejected droplets obtained with a high-speed camera during printing. Several observations can be made from this plot. First, both the convex and cylindrical designs exhibit a lower droplet volume and thus a higher acoustic force $F_a$ than the smooth design. The convex design does not have any data for voltages above 160 V because droplet detachment becomes unstable and clogging occurs at or above this voltage. Between 70 V and 160 V, however, both the cylindrical and convex designs exhibit similar values. The cylindrical design has a strong acoustic antinode at the nozzle opening due to its geometry and, absent perfect centering of the nozzle, the exiting droplet may be strongly attracted toward the side (that is, away from the center of the chamber outlet). In the smooth design, the acoustic antinode may be weaker and farther from the center as the nozzle opening widens. As revealed in FIG. 9, the smooth design exhibits a weaker acoustic field, but it may have advantages in terms of ease of use and printing precision.

In addition to an apparatus for acoustophoretic printing, a method of acoustophoretic printing is described herein. The method may entail generating an acoustic field at a first end of an acoustic chamber fully or partially enclosed by sound-reflecting walls. The acoustic field interacts with the sound-reflecting walls and travels through the acoustic chamber, ultimately being transmitted through a chamber outlet at a second end of the acoustic chamber. The acoustic field is enhanced in the chamber outlet, which functions as a sub-wavelength resonator or subWAVE, as explained above. An ink is delivered into a nozzle positioned within the acoustic chamber that has a nozzle opening projecting into the chamber outlet. The ink travels through the nozzle to the nozzle opening and is exposed to the enhanced acoustic field in the chamber outlet. A predetermined volume of the ink may thus be ejected from the nozzle opening and out of the acoustic chamber. The chamber outlet or subWAVE may achieve a resonant condition that strongly enhances the acoustic field and provides an acoustic force to facilitate droplet detachment and ejection from the chamber. The acoustic resonance may be referred to as a Fabry-Perot resonance, as explained above.

Advantageously, the acoustic field comprises a velocity antinode at the second end of the acoustic chamber adjacent to the chamber outlet. The acoustic field may further comprise a plurality of the velocity antinodes between the first end and the second end of the acoustic chamber. To exploit the presence of multiple velocity antinodes, the acoustic chamber may include a plurality of chamber outlets, where each chamber outlet is positioned adjacent to (e.g., below) one of the velocity antinodes, and a plurality of the nozzles, where each nozzle has a nozzle outlet projecting into one of the chamber outlets.

The acoustic field may be generated by an emitter, which may take the form of a piezoelectric transducer, a metal oscillator or another source of sound waves. A suitable driving frequency may be in the range from 1 kHz to 2 MHz, and more typically from 20 kHz to 250 kHz. At a suitable driving frequency, a resonant condition corresponding to a high acoustic pressure may be achieved in the chamber outlet.

The acoustic field generated in the acoustic chamber may be highly dependent on the dimensions of the acoustic chamber as described above and in the examples. Consequently, controlling the dimensions of the acoustic chamber may provide a tool for adjusting and selecting the size of the ejected droplets. Additionally, for a given size and/or geometry of the acoustic chamber, the size of the ejected droplets may be controlled by varying the emitter amplitude.

Figure 10A:
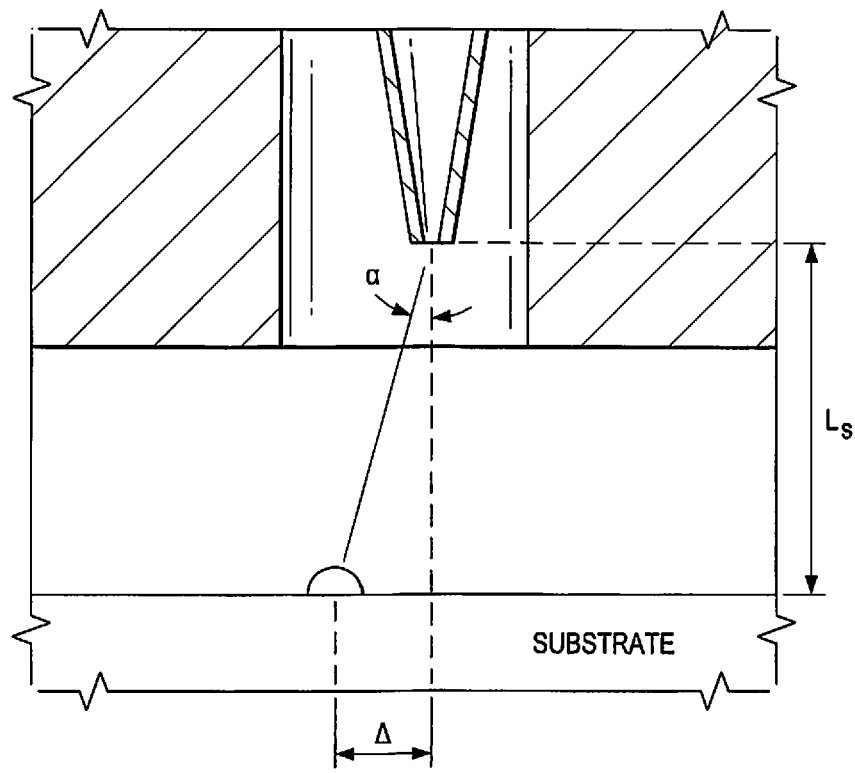
FIGS. 10A-10C show droplet position accuracy achieved by acoustophoretic printing with a nozzle diameter (nozzle opening) d of 80 µm and using an ink comprising 50% glycerol in water. Drop trajectory errors are presented as standard deviations and the scale bar is 2 mm.
Figure 10B:
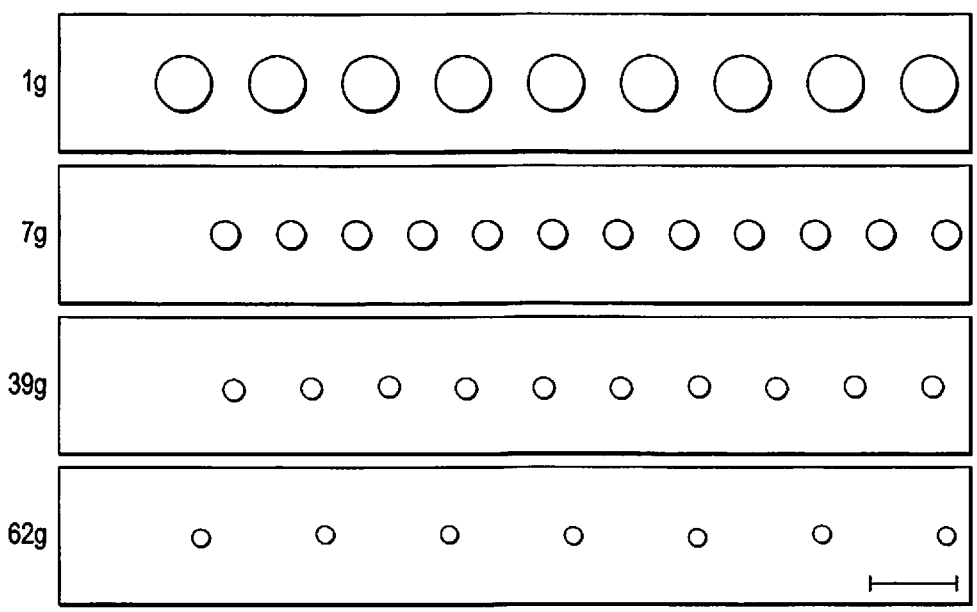
Figure 10C:
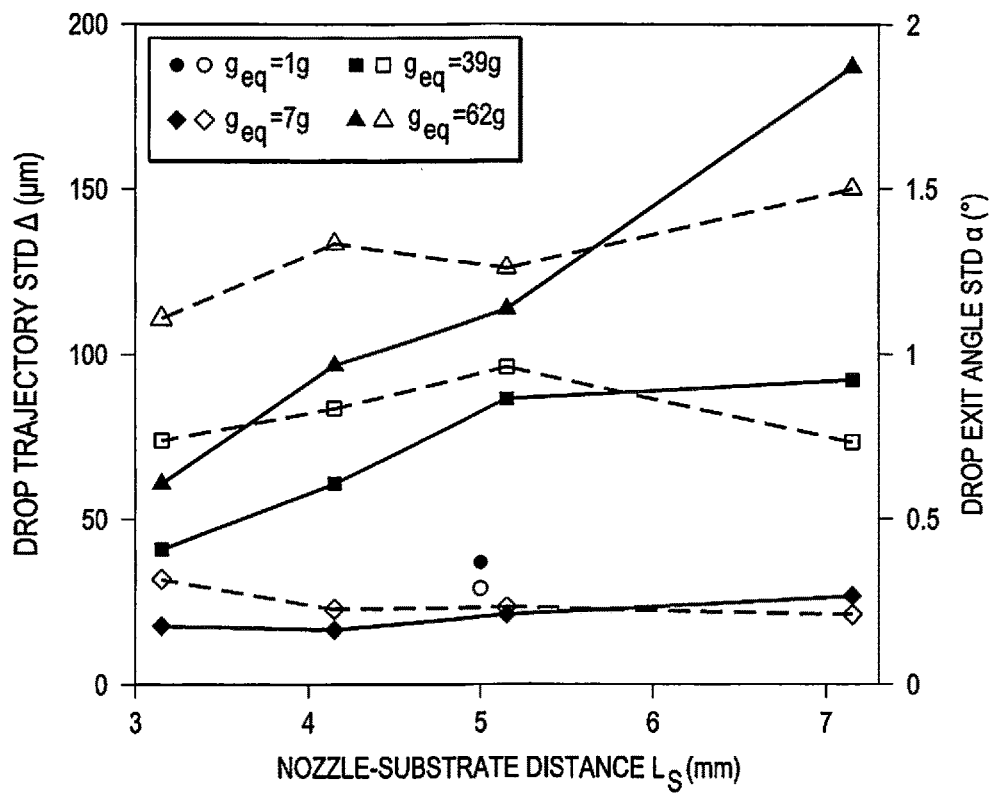
Figure 18A:
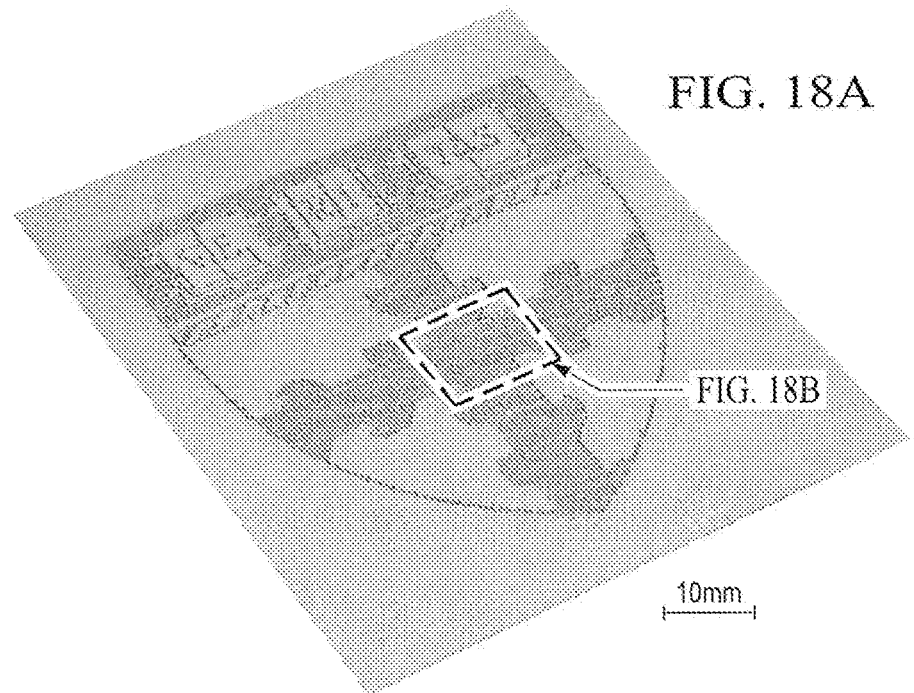
FIGS. 18A-18C show a rasterized picture prepared by acoustophoretic printing at different magnifications, where fluid dispensing is synchronized with substrate movement to allow for spatial control of droplet deposition.
Figure 18B:
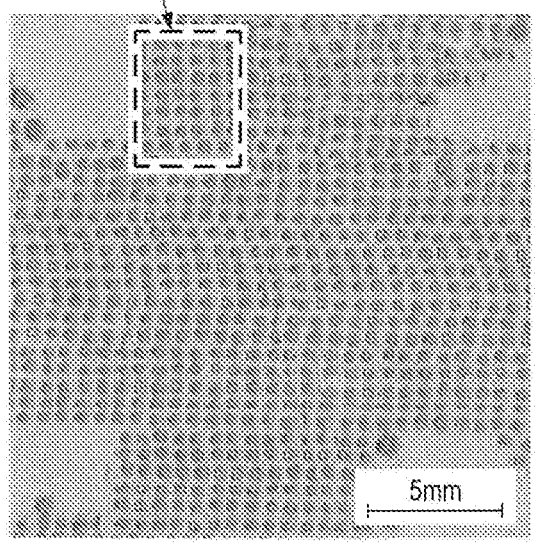
Figure 18C:
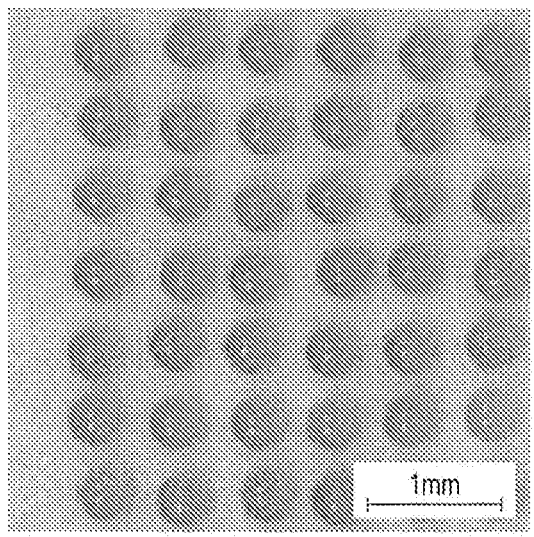

Droplet generation, ejection (or outcoupling) from the acoustic chamber, and droplet trajectory control are important aspects of acoustophoretic printing. Printing accuracy is influenced by the distance between the nozzle opening and the substrate, and the magnitude of acoustophoretic forces. Ballistic ejection of the droplet is confirmed by the exit angle error, which remains mostly constant at different nozzle-substrate distances, as shown in FIGS. 10A-10C. Its value from about 0.2° to about 5° compares well with experimental inkjet apparatuses. The apparatus described herein can achieve a droplet position error variation of about 100 µm or less for strong acoustophoretic fields. This error may be decreased linearly by increasing the operation ultrasonic frequency, which would allow the size of the subWAVE to be linearly decreased (5.3 mm) and thus the minimum substrate-nozzle distance could be decreased. Indeed, a present exemplary system is based on a 25 kHz driving frequency that allows a minimum nozzle opening-substrate distance of 3.15 mm. Position accuracy below about 25 µm may be achieved by using driving frequencies above 100 kHz, which are commonly found in ultrasonic actuators. The robustness of the acoustophoretic printing apparatus is demonstrated by printing a large rasterized image of 10 cm×7.5 cm in size, as shown in FIGS. 18A-18C. Printing speeds in the 1-10 mm/s range are typically achieved, although a much wider range of printing speeds is possible (e.g., from about 0.1 mm/s to about 1 m/s).

Possible applications for acoustophoretic printing include optics, microfluidics, bioprinting, food manufacturing and stretchable electronics. Given the wide range of ink material capability, drop-on-demand (DOD) features, and robustness, acoustophoretic printing can be employed to realize a diverse array of materials and products. FIGS. 19A-19D highlight the versatility of acoustophoretic printing with examples from the food industry, optics, human-tissue engineering and stretchable electronics.

Figure 19A:
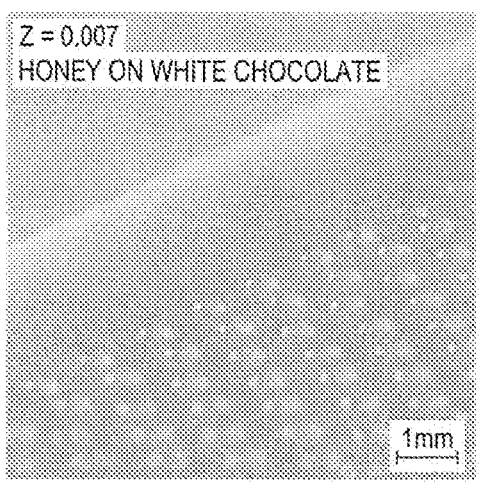
FIGS. 19A-19D illustrate successful acoustophoretic printing of a variety of inks having values of Z over a wide range, including food products, polymers, biomaterials, and electrically conductive materials, respectively.

Additive manufacturing for food is a growing and novel market and field of research, while honey represents a typical lay example of a viscous fluid; being able to DOD print such a fluid without any kind of chemical, physical, thermal or electric adulteration represents a litmus test of the process described in this patent document. FIG. 19A shows honey drops (Z=0.007) on white chocolate as deposited in a regular pattern by acoustophoretic printing at room temperature (21° C., μ=25 Pa·s). Droplets are about 580 microns in size with a footprint of 690 microns.

Figure 19D:
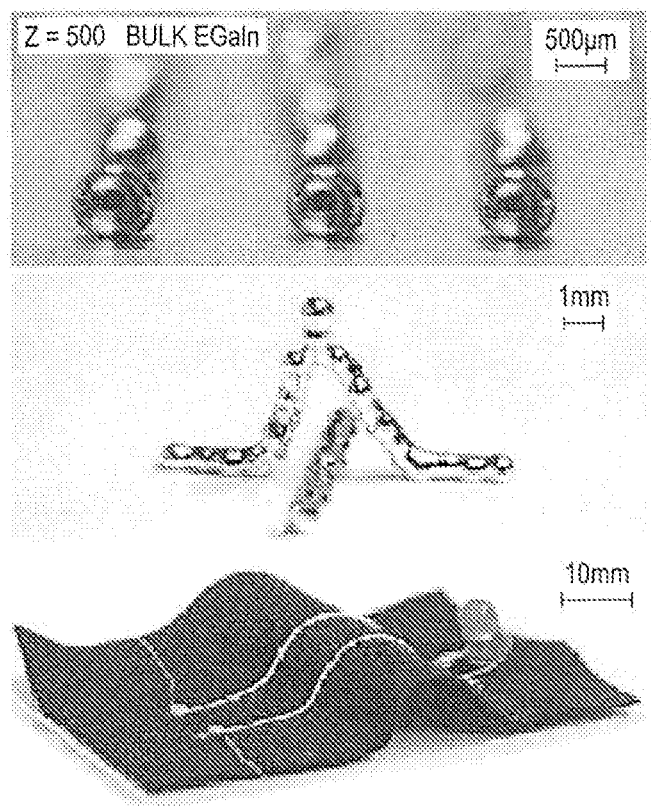
Figure 19B:
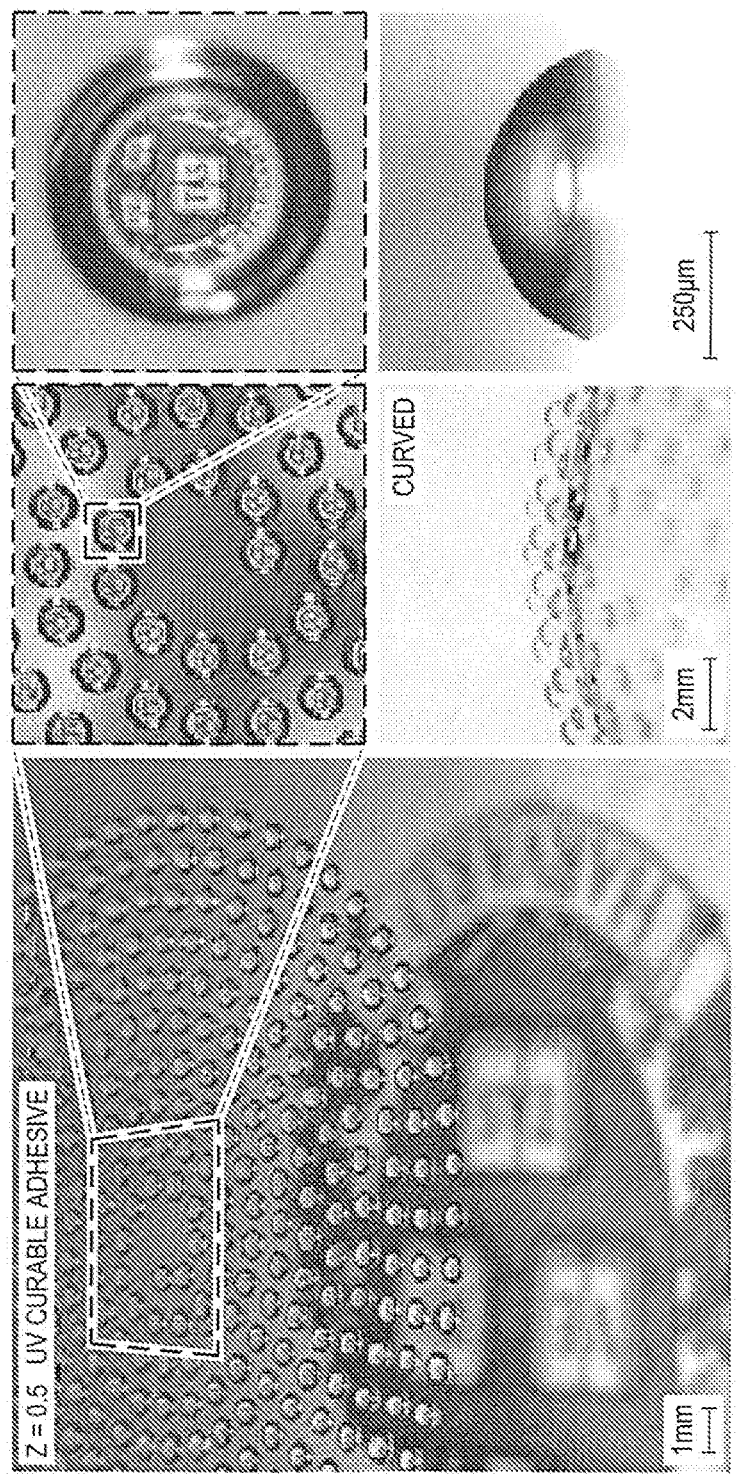

Compound eyes are well known for their infinite depth of field and wide field of view. Nevertheless, their artificial counterparts—microlens arrays—are characterized by cumbersome fabrication, especially in 3D forms. FIG. 19B shows a microlens array printed in a spiral fashion with a high degree of consistency between droplets (average diameter=570±20 μm, contact angle 74±4°) of an ultra-violet (UV) light-curable transparent adhesive (Z=0.5, NOA60, μ=300 mPa·s). The DOD, contactless printing ability of acoustophoretic printing allows arbitrary patterning of the adhesive droplets on conformal and non-conformal substrates, as shown.

Figure 19C:
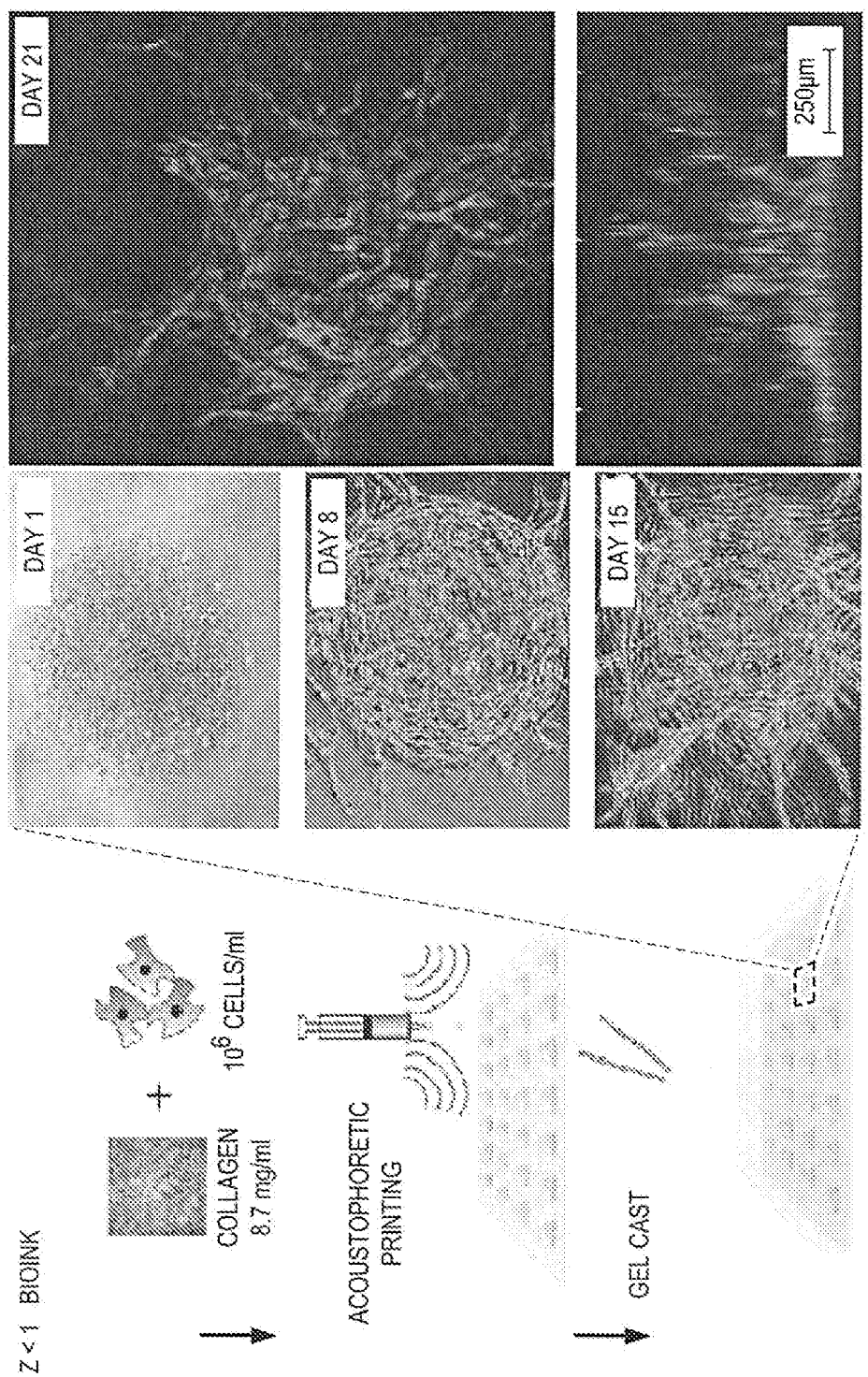

In human-tissue engineering, a prototypical printing of human mesenchymal stem cells (hMSC) in collagen is presented in FIG. 19C. Collagen is widely used in tissue engineering since it is a natural extracellular matrix material (ECM). Nevertheless, its use in the field of bioprinting comes with multiple problems, since its viscosity is subject to change due to fibril aggregation. FIG. 19C shows how, due to the ink-viscosity independency of the acoustophoretic process, drops of an extremely high-concentration collagen solution (5 mg/ml; Z<1) and stem cells can be ejected and patterned during a long period of time (1 to 2 hours) on a substrate at room temperature without compromising the ejected volume or hindering the printing process. In the acoustophoretic patterning of hMSCs, pure highly-concentrated collagen (5 mg/ml) may be neutralized (pH≈7) and mixed with hMSCs at $10^6$ cells/ml. The prepared biomaterial may be kept at about 6° C. and printed at room temperature (21° C.) onto glass cover slips. The printed structures may then be incubated for 30 minutes to ensure collagen fibril aggregation. Finally, a gelatin/fibrin matrix is casted over them. After incubation, the cells proliferate and within 3 weeks they form a branching network. The successful growth of three-dimensional networks of hMSCs illustrates that acoustophoretic printing is extremely gentle, so the cells remain viable. Furthermore, positive staining of CD90 indicates that they maintain their multipotent state after printing.

In the high Z-number range, low viscosity and high surface tension inks such as liquid metals can be printed. FIG. 19D shows acoustophoretic printed features of bulk eutectic gallium indium (EGaIn) which has Z=500. Bulk EGaIn is DOD printed at room temperature using the method and apparatus described in this disclosure to form individual drops, self-standing structures, and functional circuits on stretchable fabric, as shown. While being extensively used in molding, EGaIn is very difficult to extrude or eject, since it promptly forms an oxide layer at the interface with air. Prior to now, pure EGaIn has not been printed in contactless, dropwise fashion. Using acoustophoretic forces, there is no need for intermediate steps to prepare the liquid metal, such as processing it into a nanoparticle colloid. Single drop, self-standing three-dimensional structures and functional conducting circuits on a stretchable fabric can be easily achieved by means of acoustophoretic printing.

As the above examples show, the ink may be successfully printed over a wide range of Z values (e.g., from 0.001 to 1000). In specific embodiments, the ink may have a value of Z from 0.001 to less than 1, from 1 to 10, or from greater than 10 to 1000. Among the large range of inks that may be successfully printed are synthetic and naturally-derived biocompatible materials with or without cells (e.g., human cells such as stem cells, primary cells or other cell types), electrically or ionically conductive materials such as liquid metals (e.g., EGaIn), and polymers such as adhesives, hydrogels, elastomers and others. It should be noted that some polymers may be biocompatible and/or conductive. For example, polymers such as polyaniline and ionically conductive hydrogels are intrinsically conductive, and other "extrinsically conductive" polymers may be rendered conductive by additives, such as metal particles. Polymers such derived from collagen, hyaluronate, fibrin, alginate, agarose, chitosan or gelatin, for example, may be biocompatible. Suitable inks may also or alternatively include drugs, pharmaceutical agents and/or food products.

Physical Principle

Figure 11A:
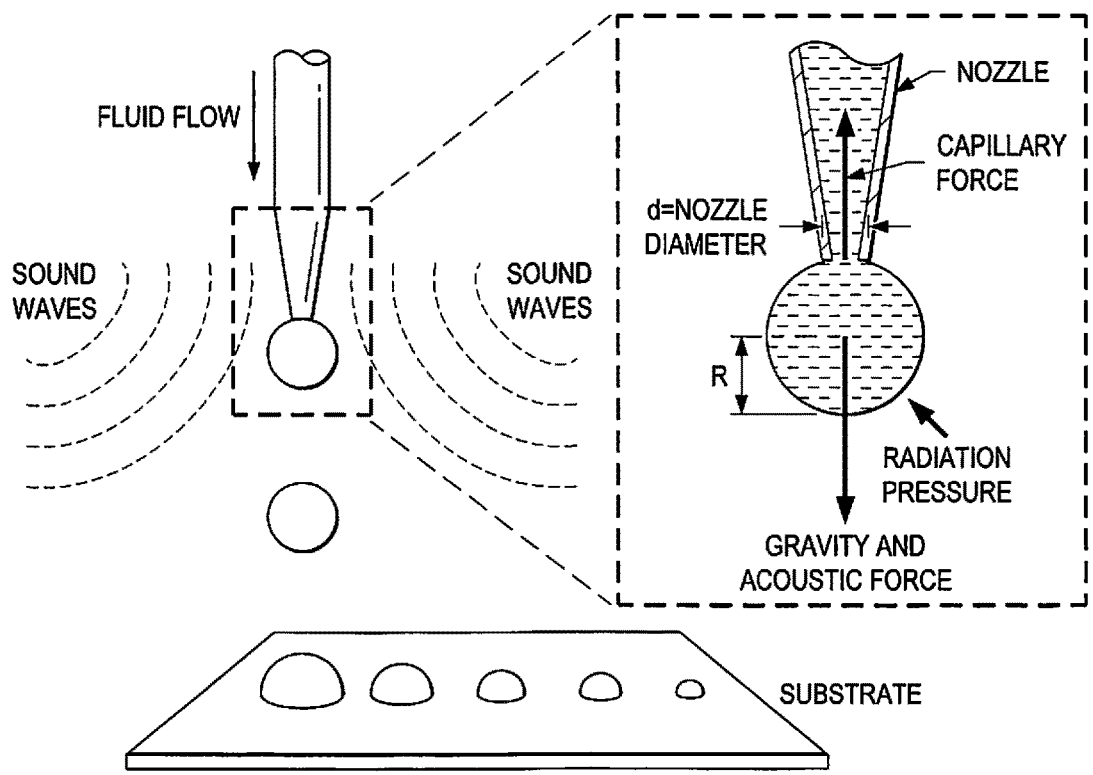
FIG. 11A shows a schematic of droplet detachment in an acoustic field, where radiation pressure acts as an additional force to overcome the capillary interaction between pendant droplet and nozzle.

To understand the advantage of employing a high-intensity acoustic field during 2D or 3D printing, the basic physical principle behind (ink) droplet detachment is explained here. Referring to FIG. 11A, a droplet of radius R detaches from a nozzle of diameter d when an applied external force $F_e$ overcomes the nozzle capillary force $F_c=\pi\sigma d$. When only the gravitational force $F_g=V\rho g$ is present, the detachment occurs when $F_c=F_g$, with V being the droplet volume, and g the gravitational acceleration. For a given liquid and a nozzle diameter, the corresponding liquid volume V* may be represented by $V^*=\pi d\sigma/\rho$.

In such a system, the flow through the nozzle is decoupled from droplet detachment. The gravity force acts as a body force and an external force compared to the nozzle/reservoir system. Viscosity plays little role in this quasi-static approximation, and it does not appear in the equilibrium equation $V^*=\rho/\sigma/\rho$. This decoupling allows ink droplets of practically any viscosity to be ejected from a nozzle when dealing with Newtonian fluids.

Figure 11B:
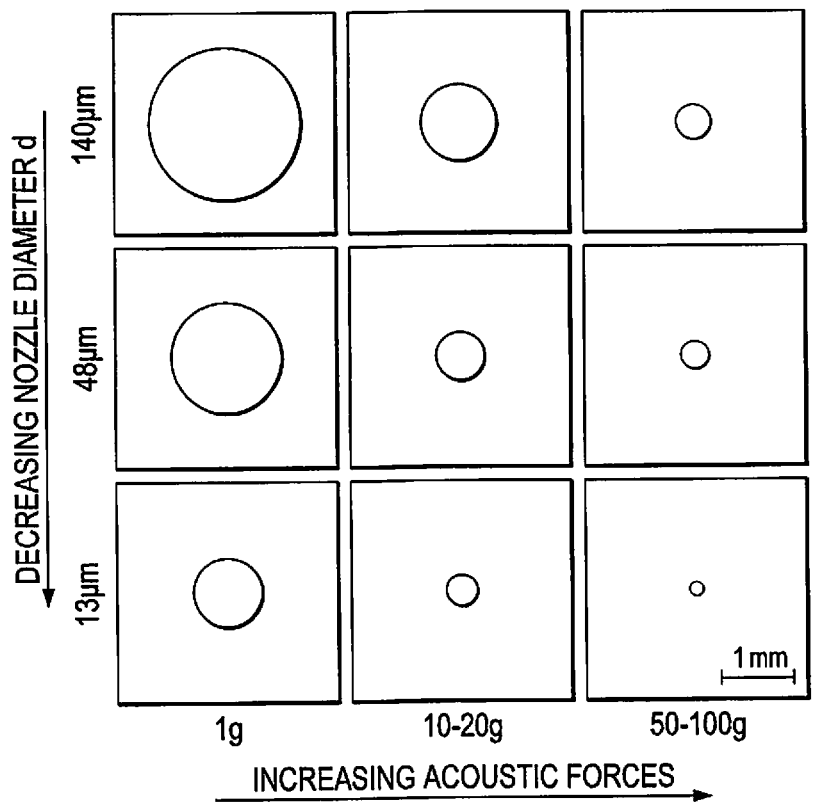
FIG. 11B shows the relationship between increasing acoustic forces, decreasing nozzle diameter d and droplet size, where water is the ink in this example.
Figure 11C:
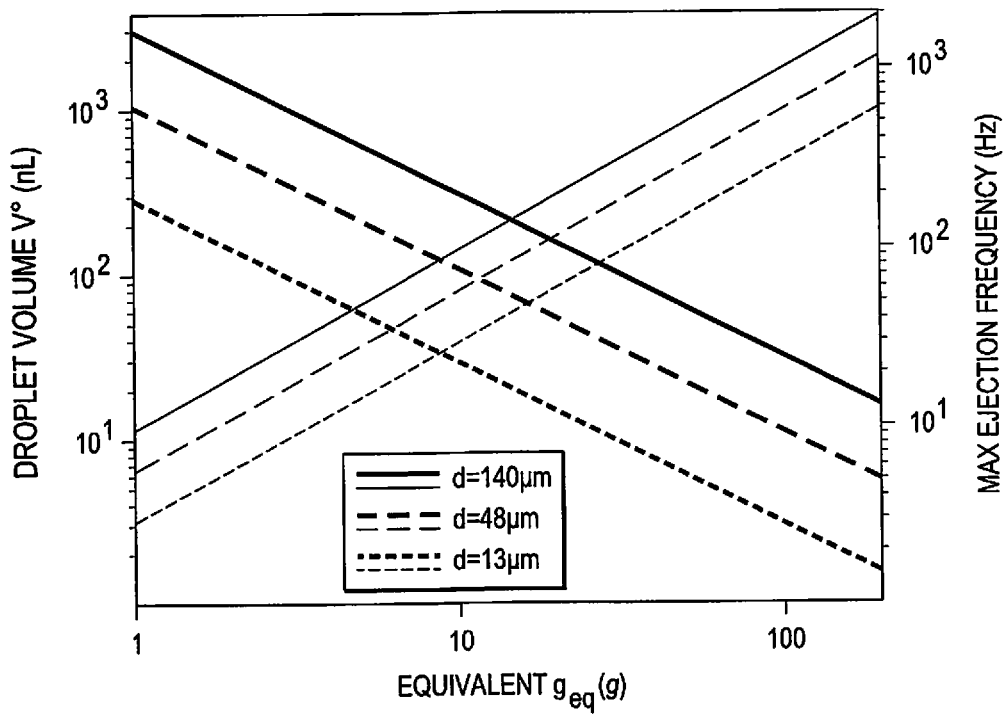
FIG. 11C shows droplet volume and maximum ejection frequency as a function of $g_{eq}$.

To decrease the droplet size at detachment, two options are possible: the fluid properties, σ/ρ, may be acted on, or d may be acted on. The former approach may be more limiting, since σ and ρ are usually of the same order of magnitude for most liquids of interest and, additionally, it is not consistent with a material-independent ejection concept. The nozzle diameter d can be varied from the millimeter size range down to the submicron size range, allowing for a linear decrease of V*, as illustrated in FIGS. 11B-11C. Unfortunately, at small d, physical limits due to viscous and interfacial forces may hinder liquid ejection. In fact, when the nozzle diameter decreases, Laplace pressure losses strongly increase for Newtonian fluids, leading in some cases to prohibitively large pressure drops. Additionally, when dealing with colloidal inks, the nozzle is preferably at least an order of magnitude larger than the dispersed particle diameter to avoid clogging. The concept presented here uses nonlinear acoustic forces (acoustophoresis) to provide an additional variable to control the size of the detached droplet.

The force on the droplet arises from the radiation pressure, which is a nonlinear effect of the acoustic field. Acoustophoretic forces are essentially material independent when handling liquid or solid samples in air. In particular, when dealing with spherical objects (i.e. a drop) in an acoustic standing wave configuration, the acoustophoretic forces scales as $F_a \propto R^3 p^2 \propto V p^2$, with p being the acoustic pressure. This scaling highlights three important aspects: 1) no property information is needed regarding the sample material since the forces are material independent; 2) the acoustic forces are strongly dependent on the acoustic pressure; 3) since gravitational forces are also proportional to V, an equivalent (augmented) acoustic acceleration $g_a$ can be introduced.

$$F_c = \pi \sigma d = F_g + F_a = V^* \rho (g + g_a) \rightarrow V^* = \pi d \sigma / \rho g_{eq} \quad (1)$$

Equation 1 illustrates acoustophoretic droplet generation in all its simplicity and power. Since $F_a \propto g_a \propto p^2$, for any liquid or nozzle $V^* \propto 1/p^2$. FIG. 11B shows the level of control of the detached droplet size by acting on the acoustic pressure p: more than two orders of magnitude in volume for the same nozzle size. Eq. 1 is valid under the assumption of a flow through the nozzle q not exceeding the jet limit, $q < \pi (d^3 \sigma / 2 \rho)^{1/2}$, presenting some similarity with co-flow droplet generation in microfluidics. Accordingly, an ejection frequency in the kHz range is possible with acoustophoretic printing.

Figure 12:
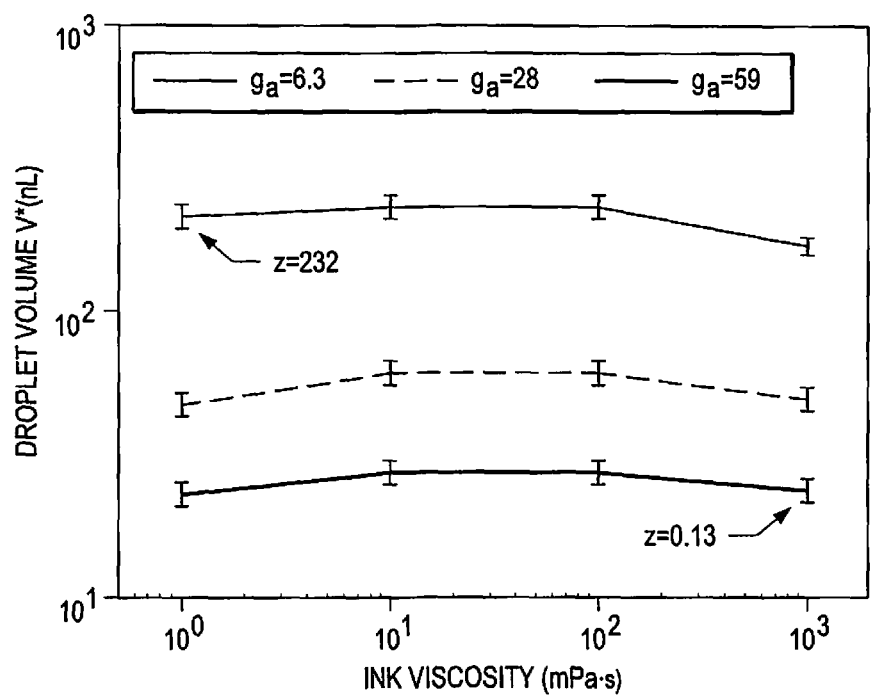
FIG. 12 shows the dependence of acoustophoretic droplet generation on the viscosity of the ink.

With its inherent independence of viscous material properties, acoustophoretic printing enables droplet generation from inks of disparate classes. Acoustophoretic printing can generate droplets in a Z-range that extends the state of the art by more than four orders of magnitude; such a capability may allow a much wider swath of materials to be printed in a contactless droplet-based fashion, enabling new possibilities in the realm of functional printing. Since the droplet detachment is not dependent on interfacial breakup, acoustophoretic printing is indeed little affected by the ink viscosity. In order to showcase this characteristic, deionized water and a polymer solution (Poly Ethylene Glycol, PEG molecular weight 8000) are continuously mixed to span three orders of magnitude of ink viscosity, from $\mu=1$ mPas to 1000 mPas. FIG. 12 shows the dependence of acoustophoretic droplet generation on the viscosity of the ink. The values of $g_{eq}$ are averaged with respect to the dripping mode (1 g) and the red error bars represents the measurement error (1 pixel=9 μm); d=100 μm. For a defined acoustophoretic excitation, fluid viscosity has little influence on the ejected droplet volume V*.

Experimental and Computational Details
Acoustic Chamber Design

As discussed above, the acoustic field generated in the acoustic chamber is highly dependent on the dimensions of the acoustic chamber. Once the dimensions of the acoustic chamber are set based on the size of the emitter and the space needed for the nozzle(s), the emitter height $H_E$ and the reflector height $H_R$ can be considered.

Figure 13:
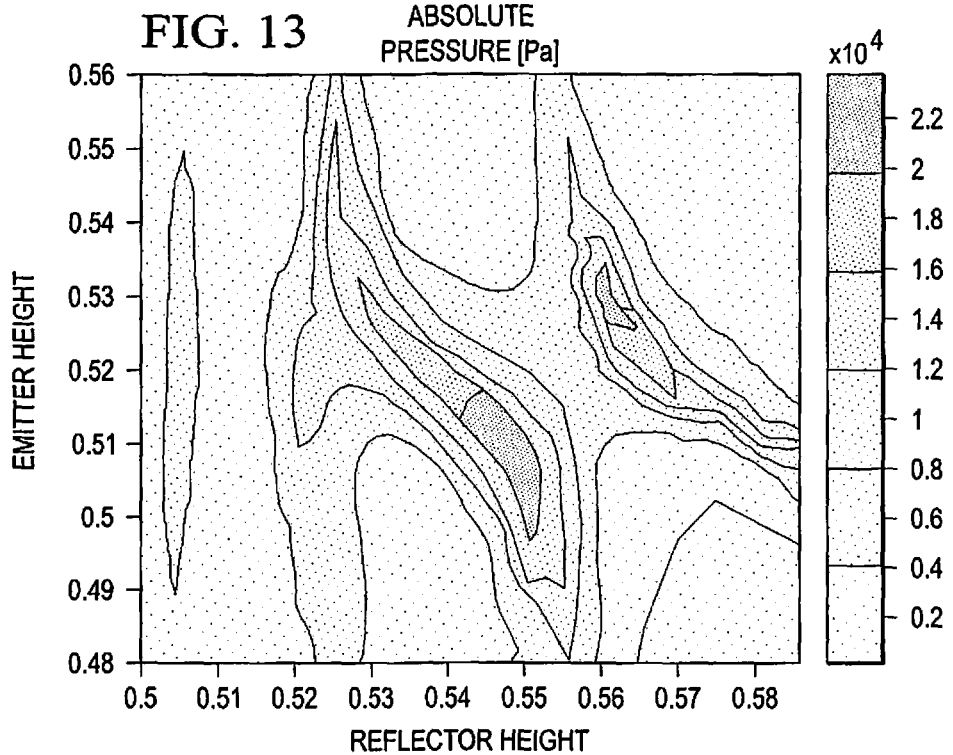
FIG. 13 shows a contour plot of acoustic pressure in Pascal as a function of $H_R$ and $H_E$, as determined by simulations.

In order to characterize the acoustic chamber and identify the optimal values of $H_E$ and $H_R$, $d_{wall}$ is set to 1.2 mm and kept constant for all measurements, corresponding to $d_{wall}=0.9\lambda$ (here, $\lambda=14$ mm). Simulations are performed where both dimensions are varied. The result is a matrix of acoustic pressure in Pascal as a function of $H_R$ and $H_E$, which is shown in a contour plot in FIG. 13. $H_E$ and $H_R$ are varied between $0.48\lambda$-$0.56\lambda$ and $0.5\lambda$-$0.58\lambda$ respectively with $0.005\lambda$ increments. The heights $H_E$ and $H_R$ are normalized by the wavelength $\lambda \approx 14$ mm of the acoustic field. Two peaks can be seen at $P_1=(H_R, H_E)=(0.55\lambda, 0.505\lambda)$ and $P_2=(H_R, H_E)=(0.565\lambda, 0.525\lambda)$, which represent the regions of highest acoustic force $F_a$ and therefore where the droplets ejected are smallest. Interestingly, the highest pressures are obtained for values of $H_E$ and $H_R$ that are not equal, i.e., $H_R \neq H_E$, and the acoustic field is shown to be very sensitive to $H_E$ and $H_R$.

Figure 14:
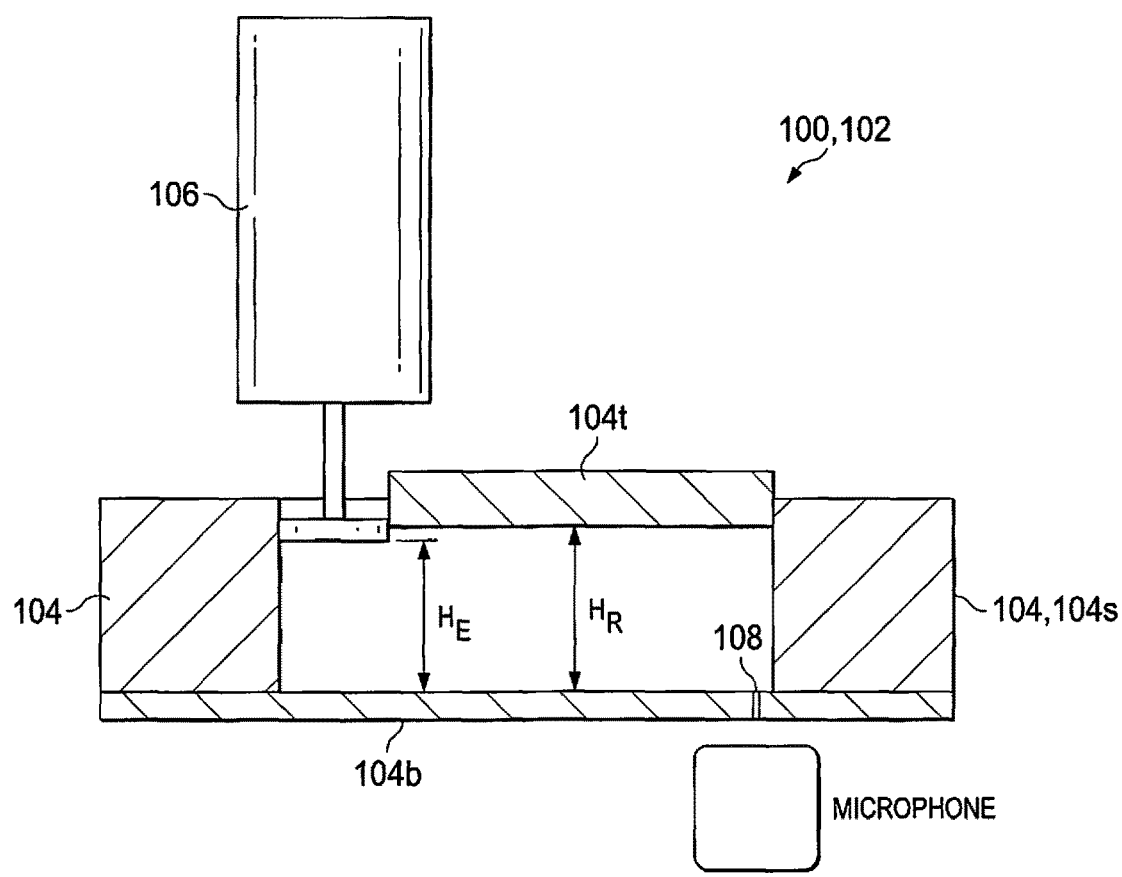
FIG. 14 shows the experimental set-up used to measure the acoustic pressure field and identify optimal values of $H_E$ and $H_R$.

The modeling of the acoustic field identifies values of $H_E$ and $H_R$ that may lead to an optimal acoustic field in the subWAVE. To study the influence of $H_E$ and $H_R$ and on the acoustic field experimentally, measurements of the acoustic pressure field are performed with a microphone. The microphone is placed outside the acoustic chamber, coaxial to the chamber outlet (subWAVE) at a distance of 8 mm from the subWAVE exit. The experimental setup used is shown in FIG. 14. The microphone is placed on a horizontal plane at the location where the acoustic field intensity is at a maximum, i.e., where the microphone output is maximized.

Figure 15:
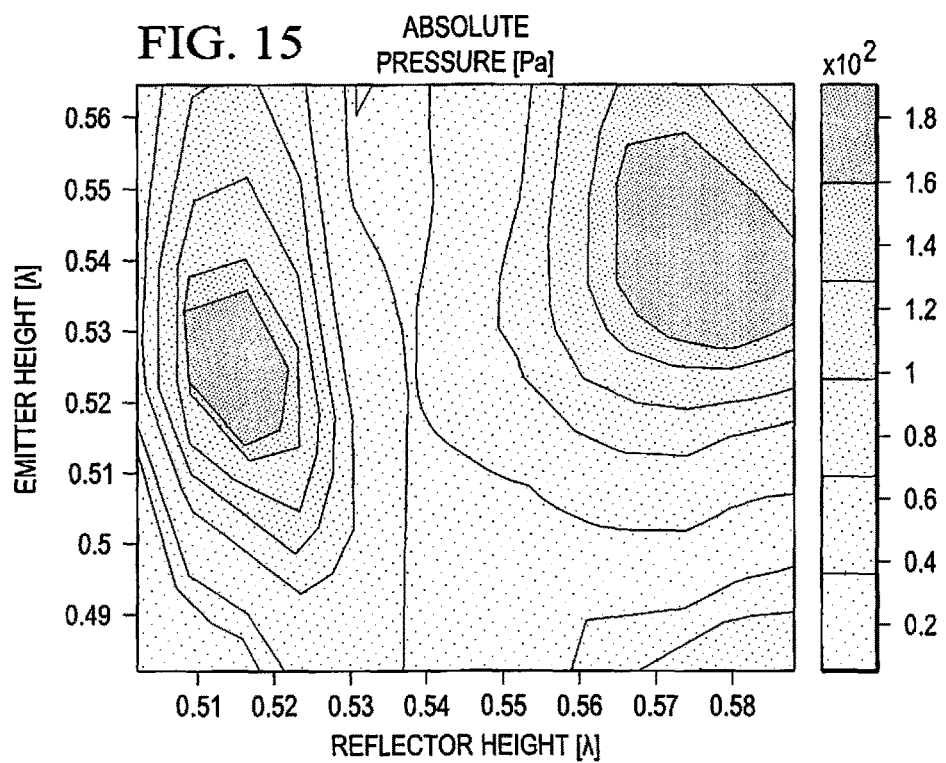
FIG. 15 shows a contour plot of acoustic pressure in Pascal as a function of $H_R$ and $H_E$, as determined by experiments.

$H_E$ and $H_R$ are varied between $0.48\lambda$-$0.56\lambda$ and $0.5\lambda$-$0.58\lambda$ respectively with $0.07\lambda$ increments. The measurements are repeated three times and the parts are disassembled and reassembled between each set of measurements. The final result is a 12×12 matrix which is a function of $H_E$ and $H_R$ and is shown in a contour plot in FIG. 15. There is a very good agreement between the microphone measurements of FIG. 15 and the simulations shown in FIG. 13. Both plots display pressure in Pascal as a function of $H_E$ and $H_R$. Two well-defined peaks can be seen at $P_1=(H_R, H_E)=(0.515\lambda, 0.523\lambda)$ and $P_2=(0.575\lambda, 0.537\lambda)$ in FIG. 15. The experimental contour plot has a very similar acoustic field distribution as obtained from the simulations. In both cases, two clear acoustic pressure peaks can be seen within the chosen emitter and reflector height ranges. The experimental data presents a slightly larger horizontal spacing between the two peaks: $\Delta H_R/\lambda=0.06$ for the microphone measurement in contrast to $\Delta H_R/\lambda=0.015$ for the simulations. On the other hand, both plots present a similar vertical spacing between the two peaks of approximately $\Delta H_E/\lambda=0.015$. An offset of around $0.015\lambda$ (1.5% of $\lambda$) in $H_E$ is observed between the experimental results and the numerical model. This offset may be due to the uncertainty in emitter height calibration. The investigation shows good agreement between microphone measurements and simulations.

Varying $H_E$ and $H_R$ provides a powerful tool to adjust and choose the size of the ejected droplets. In this study, the highest acoustic field intensity—which is believed to result in the smallest possible droplet size during printing—is found to occur with $H_E$ and $H_R$ set to $P_2=(0.575\lambda, 0.537\lambda)$. $P_2$ has a broader peak than $P_1$, providing more room for maneuver and making emitter and reflector heights adjustments easier. Given the breadth of the peak $P_2$, optimal values for $H_E$ and $H_R$ may fall in the ranges: $0.57\lambda \leq H_E \leq 0.58\lambda$, and $0.53\lambda \leq H_R \leq 0.54\lambda$.

Figure 16A:
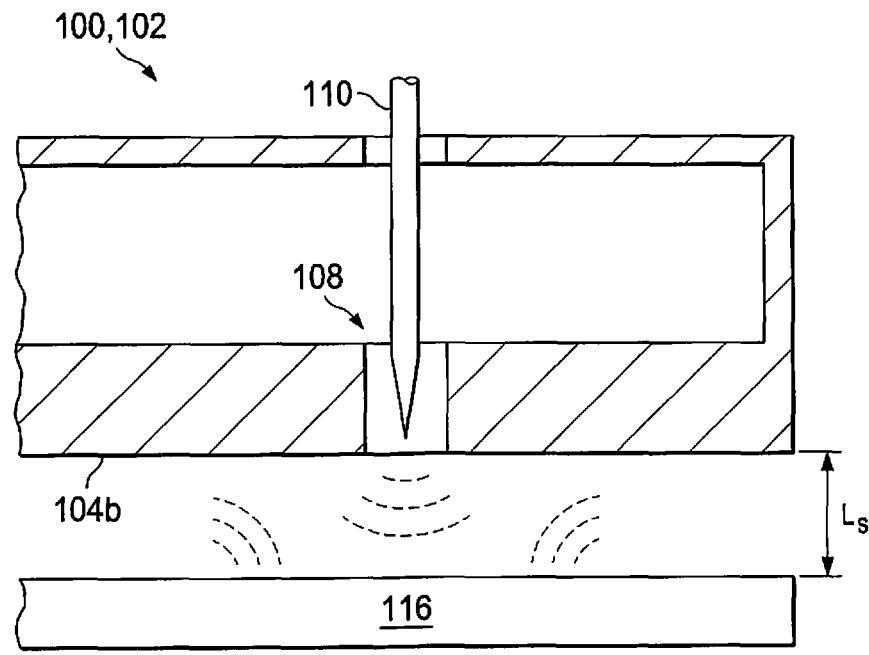
FIGS. 16A and 16C show exemplary designs of the acoustic chamber, where the sound-reflecting bottom wall has a reduced thickness in FIG. 16C.
Figure 16B:
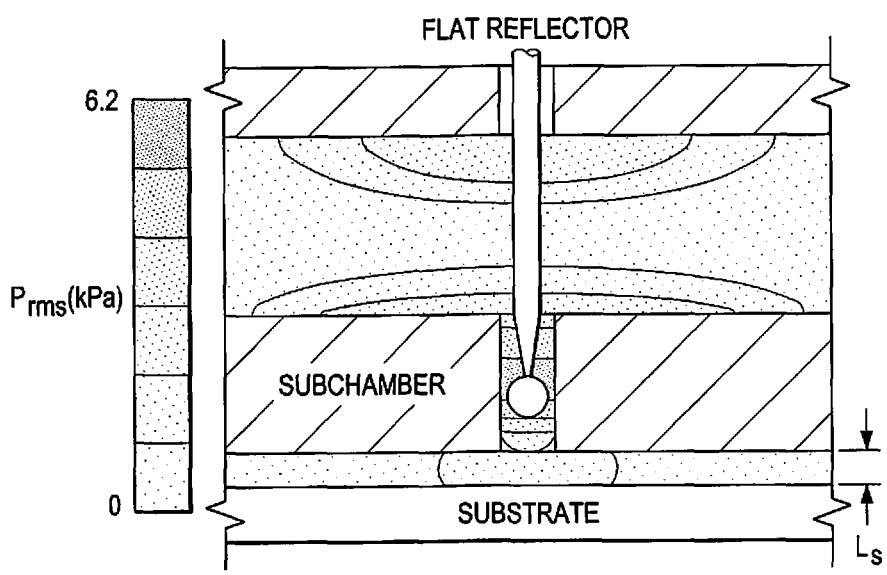
FIG. 16B and FIG. 16D show $p_{RMS}$ on the substrate and in the channel outlet as a function of $L_s$, for the acoustic chamber designs of FIGS. 16A and 16C, respectively.

FIG. 16A shows an exemplary design of the acoustic chamber with a sound reflecting bottom wall having a flat design (where the length or height of the subWAVE corresponds to the thickness of the bottom wall). The influence of $L_s$ on the subWAVE resonances is indicated in FIG. 16B. FIG. 16E shows that below $0.5\lambda \approx 7$ mm, the acoustic field strongly deteriorates for the flat design. Peaks at $0.5\lambda$, $\lambda$ and $1.5\lambda$ show the presence of resonance wavelengths and wave interference.

Figure 16C:
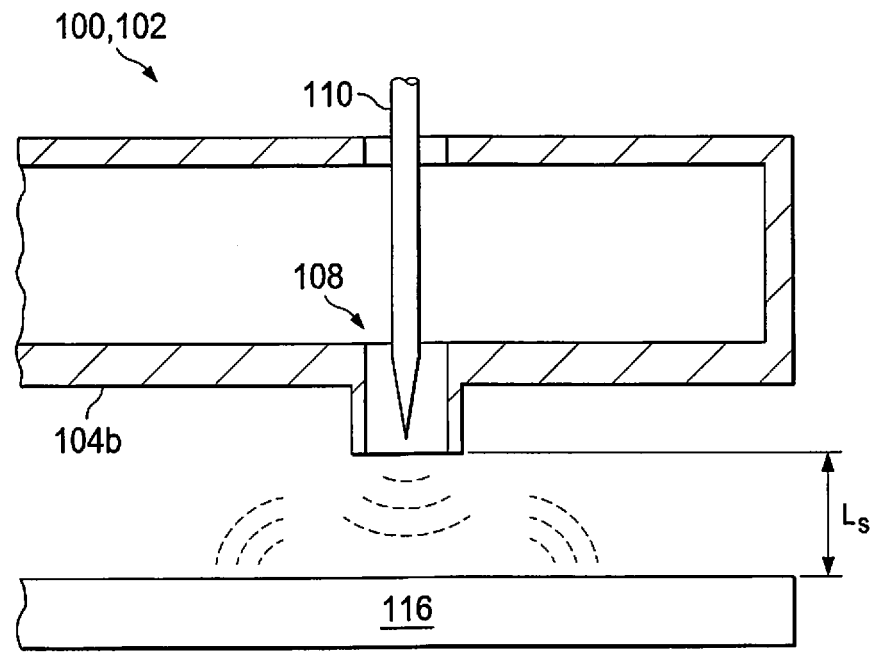
Figure 16D:
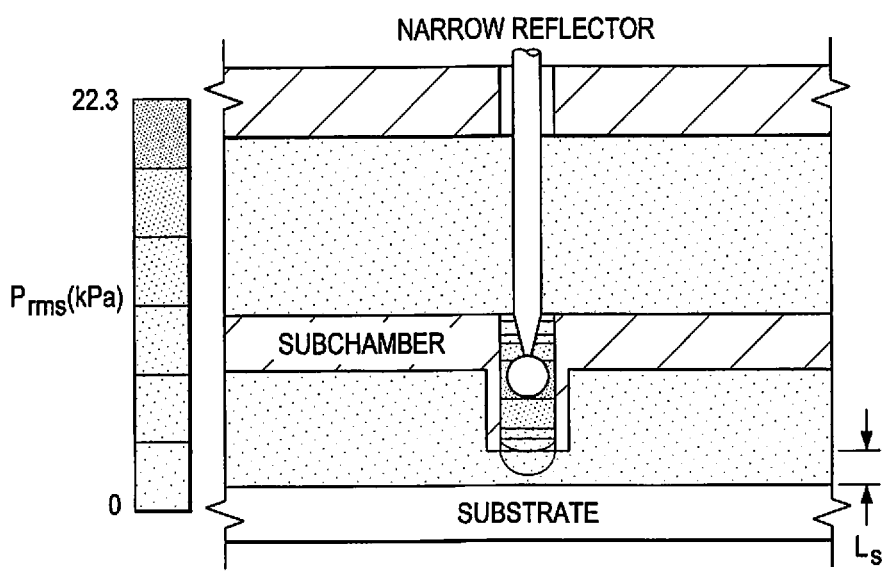
Figure 16E:
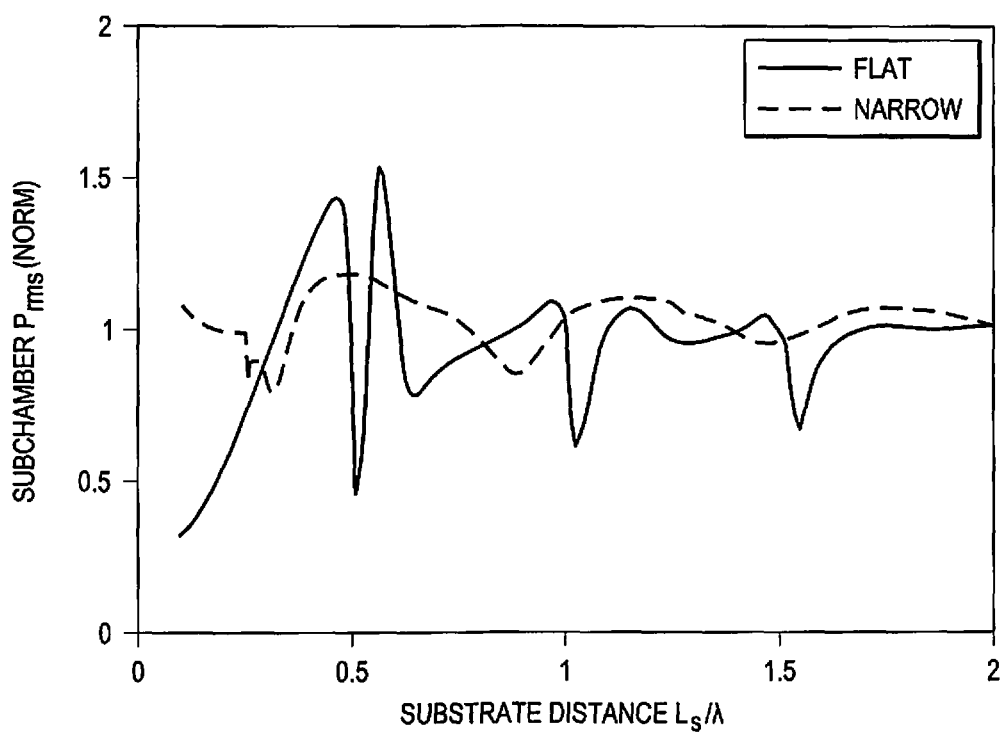
FIG. 16E and FIG. 16F show $p_{RMS}$ on the substrate and in the channel outlet as a function of $L_s$.

An alternative design is shown in FIG. 16C, which allows for a reduced-thickness reflecting surface. In this "narrow" design, the channel outlet includes an outlet portion extending beyond the sound-reflecting bottom wall. Thus, the length or height of the subWAVE exceeds the thickness of the sound-reflecting bottom wall. In such a configuration, it is possible to decouple the subWAVE and the substrate, even at low distances $L_s < 0.1\lambda$. FIG. 16B and FIG. 16D show simulations of both flat and narrow designs for a given distance $L_s$. A typical value of $L_s$ for printing is in the range of 6-8 mm. The root mean square pressure $p_{RMS}$ is plotted and a noticeable difference can be seen in maximum intensity (6.2 kPa and 22.3 kPa respectively) in the channel outlet. The narrow design of FIG. 16C exhibits $p_{RMS}$ values almost four times higher than the flat design of FIG. 16A.

Figure 16F:
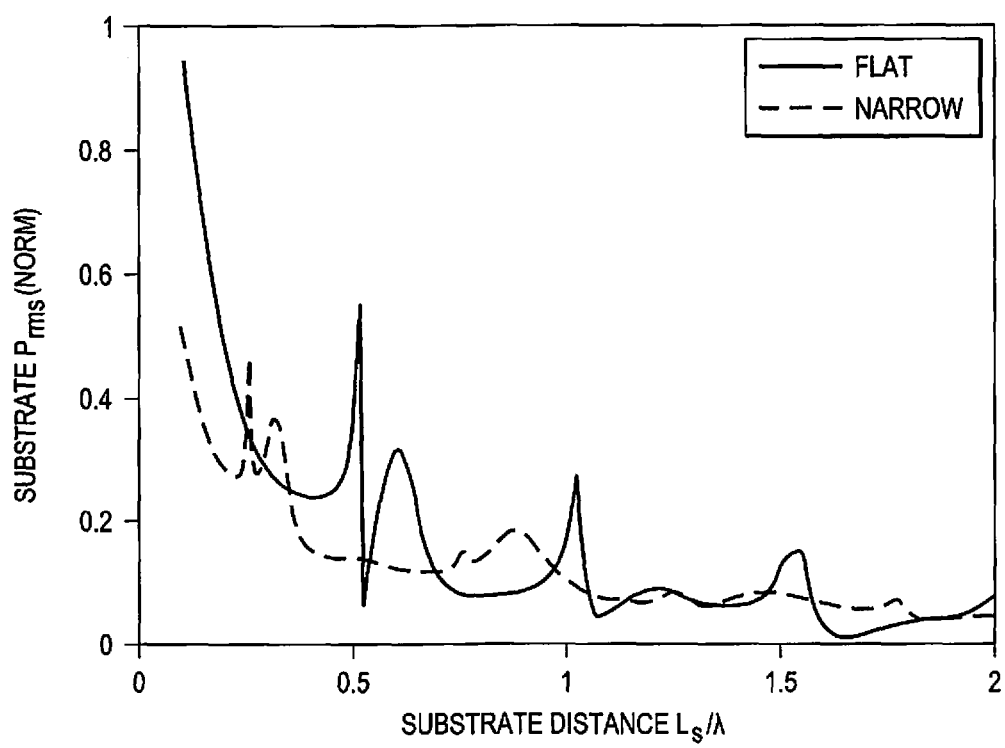
Figure 17:
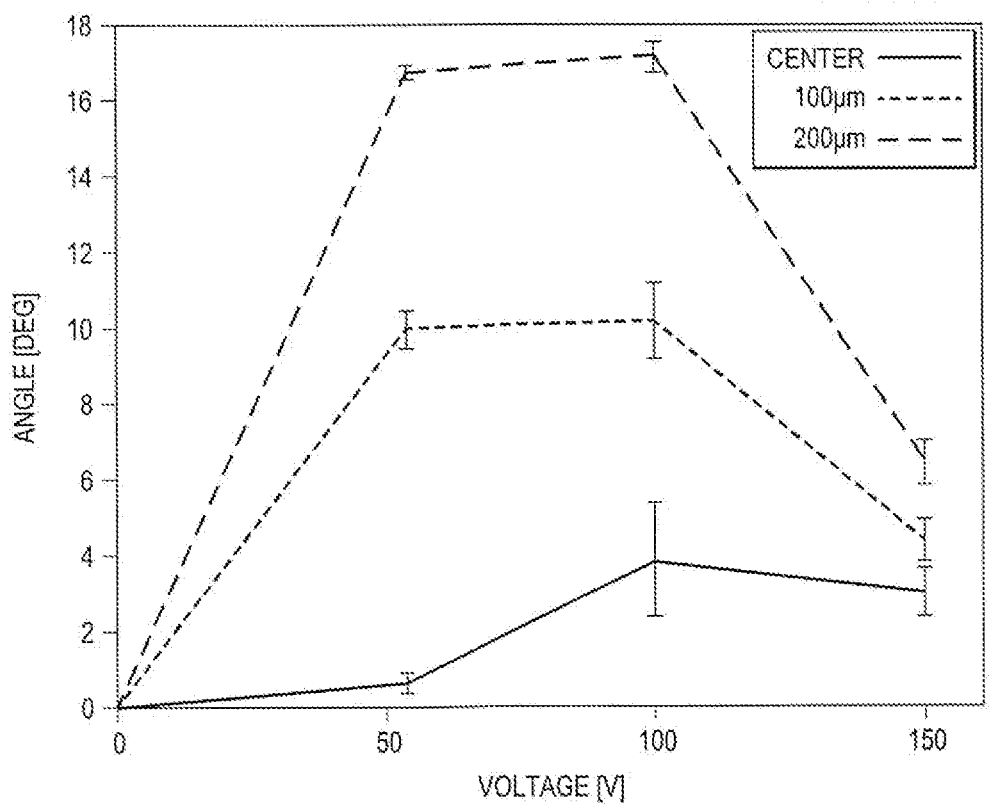
FIG. 17 shows a plot of exit angle of ejected droplets as a function of voltage for different radial positions of the nozzle inside the chamber outlet.

FIG. 16E and FIG. 16F show $p_{RMS}$ on the substrate and in the channel outlet as a function of $L_s$. The thin-walled narrow design exhibits a smoother curve in both plots than the flat design, where resonance peaks can be observed. In both plots, a noticeable difference can be seen for $L_s \leq 0.5\lambda$. In the experimental setup in use, the acoustic frequency f is about 25 kHz and the wavelength is about 14 mm. For the flat design, simulations show a deteriorating acoustic field below $L_s$=7 mm. On the other hand, as mentioned above, the narrow design can be employed successfully at distances as low as $L_s$=0.1$\lambda$=1.4 mm.

Experiments indicate that the position of the nozzle opening within the chamber outlet can influence the trajectory of the ejected droplet. In a series of experiments, a nozzle (d=1 mm) is placed in the center of the subWAVE ($d_h$=2 mm) at a height 2 mm from the exit 114 and translated in a radial direction. The nozzle takes three radial positions: center (0 μm), 100 μm from the center, and 200 μm from the center. The maximum nozzle displacement is 500 μm, at which point the nozzle touches the wall of the SUBWAVE. For displacements above 300 μm, clogging is occasionally observed. Ejected droplets are filmed and the movies are later analyzed using a custom Matlab© code that extracts information such as the droplet diameter and position. FIG. 17 shows the angle of droplets for the above-mentioned positions and for different voltages. Each data point includes a standard deviation of the angle, which is important for printing precision.

The data show, as expected from simulations, that the droplet's trajectory is altered by the acoustic field as the nozzle is moved away from the center of the chamber outlet. For example, if the nozzle is displaced to the right, the trajectory of the droplet is moved to the right. It is further noted that the angle of ejection increases as the nozzle gets closer to the wall. This corresponds very well to the simulations since $v_{RMS}$ increases closer to the wall. It is interesting that the angle increases with the voltage up to 100 V but decreases at 150 V. At 150 V, the droplet's speed becomes large enough to counterbalance the effects of $v_{RMS}$ and the droplet has a more vertical trajectory.

Ideally, each droplet has the same exit angle and, if the substrate is moved straight, the printed droplets form a perfect straight line. However, the exit angle of successive droplets is not necessarily constant. In some cases, it may be advantageous to have as little exit angle variation as possible, in other words, to reduce the variance of the exit angle. FIG. 17 shows that, in some cases, the variance of the angle decreases as the angle increases. Taking 100 V, for example, it can be seen that the variance decreases as the nozzle is displaced. This effect may be used to increase the printing precision at certain intermediate voltages, such as 100 V.

Displacement of the nozzle (and thus the nozzle opening) within the chamber outlet may be a very powerful tool to control the trajectory of the droplet. Using a micrometric stage for the nozzle displacement, it may be possible to precisely choose the exit angle and therefore the impact location. FIG. 17 shows a range of angles between 0°-17°. The geometry of the chamber outlet and the position of the nozzle impose a maximal exit angle before the droplet touches the wall. Taking a nozzle displacement of 200 μm, a droplet diameter of 300 μm and considering a straight trajectory, the maximum angle is $\alpha_{max} \approx -26°$. For a displacement of 200 μm and a voltage of 100 V, an angle of 17° is observed. This value may increase for displacements larger than 200 μm. Angles up to 35° are observed for large displacements (approximately 300 μm).

Experimental Set-Up

The experimental set-up includes a sound source, an acoustic chamber and a fluid (ink) dispensing system.

Sound system: A magnetostrictive transducer (Etrema C18A) excites the resonant mode of an emitter (designed in-house). The resonance frequency of the system is 26.460 kHz. The transducer is driven by a sinusoidal signal at the resonance frequency of the system of 26.460 kHz and amplified to a maximum value of 115 V (Peavy CS4080).

Acoustic chamber: The acoustophoretic printing apparatus was designed and manufactured in-house with multiple acrylic parts. To allow for easy nozzle insertion, the acoustic chamber is rectangular, measuring 15 mm×65 mm×7.5 mm. The emitter is at one end and the chamber outlet is at the other end. The subwavelength chamber outlet takes the form of a cylindrical bore of 2 mm in diameter and 5.5 mm in length or height.

Fluid dispensing system: Experiments were performed with two positive displacement systems, including a syringe pump (Harvard apparatus) and a Nordson EDF2800 Ultra. Both systems utilize a Luer-lock connection to the nozzle. Tapered glass nozzles are manufactured in-house with a pipette puller (Sutter P-1000) and connected to a Luer-lock connector with epoxy glue. The nozzle tips are treated with a hydrophobic coating to reduce wetting.

Numerical Model

An axisymmetric linear acoustic model was implemented with an FEM solver to calculate the acoustic field inside the subWAVE. The acoustic force was calculated with both the Gor'kov potential model and the surface integral of the radiation pressure on the sphere.

Although the present invention has been described in considerable detail with reference to certain embodiments thereof, other embodiments are possible without departing from the present invention. The spirit and scope of the appended claims should not be limited, therefore, to the description of the preferred embodiments contained herein. All embodiments that come within the meaning of the claims, either literally or by equivalence, are intended to be embraced therein.

Furthermore, the advantages described above are not necessarily the only advantages of the invention, and it is not necessarily expected that all of the described advantages will be achieved with every embodiment of the invention.

The invention claimed is:

1. A method of acoustophoretic printing, the method comprising:

generating an acoustic field of wavelength A by an emitter having a longitudinal axis L and being positioned at a first end of an acoustic chamber fully or partially enclosed by sound-reflecting walls, the longitudinal axis L being aligned with a direction of oscillations from the emitter, the acoustic field interacting with the sound-reflecting walls and traveling through the acoustic chamber to a chamber outlet at a second end of the acoustic chamber, the chamber outlet being spaced apart from the emitter by a distance $d_x$ in a direction normal to the longitudinal axis L of the emitter;

delivering an ink into a nozzle positioned within the acoustic chamber, the nozzle having a nozzle opening projecting into the chamber outlet, the ink traveling through the nozzle and being exposed to the acoustic field at the nozzle opening; and ejecting a predetermined volume of the ink from the nozzle opening and out of the acoustic chamber.

2. The method of claim 1, wherein the chamber outlet comprises a cross-sectional area A and a height $H_h$, where $\pi/4 \cdot (0.01)^2/\lambda^2 \leq A \leq \pi/4 \cdot (0.2)^2/\lambda^2$ and $0.30\lambda \leq H_h \leq 0.60\lambda$ or $0.80\lambda \leq H_h \leq 1.0\lambda$.

3. The method of claim 1, wherein the acoustic field comprises a velocity antinode at the second end of the acoustic chamber adjacent to the chamber outlet.

4. The method of claim 1, wherein the acoustic field comprises a plurality of velocity antinodes between the first end and the second end of the acoustic chamber.

5. The method of claim 4, further comprising a plurality of the nozzles in the acoustic chamber and a plurality of the chamber outlets, each of the nozzles having a nozzle outlet projecting into one of the chamber outlets, and each of the chamber outlets being positioned adjacent to a velocity antinode.

6. The method of claim 1, wherein, during delivery of the ink, a radial position of the nozzle opening in the chamber outlet is changed with respect to a longitudinal axis thereof, thereby altering a trajectory of the predetermined volume of the ink.

7. The method of claim 1, further comprising a substrate disposed outside the acoustic chamber and facing the chamber outlet, the substrate moving relative to the chamber outlet at a speed of 0.1 mm/s to 1 m/s.

8. The method of claim 1, wherein the ink is selected from the group consisting of: Newtonian fluids, non-Newtonian fluids, viscoelastic fluids, yield stress fluids, polymer solutions, hydrogels, colloids, emulsions and complex fluids.

9. The method of claim 1, wherein the ink comprises a synthetic or naturally-derived biocompatible material.

10. The method of claim 9, wherein the ink includes human cells.

11. The method of claim 1, wherein the ink comprises a drug or other pharmaceutical agent.

12. The method of claim 1, wherein the ink comprises an electrically or ionically conductive material.

13. The method of claim 1, wherein the ink comprises a food product.

14. The method of claim 1, wherein the sound-reflecting walls include a sound-reflecting side wall at the second end of the acoustic chamber.

* * * * *